US006677355B1

(12) United States Patent
Conrad et al.

(10) Patent No.: US 6,677,355 B1
(45) Date of Patent: Jan. 13, 2004

(54) HYDROXAMIC ACID COMPOUNDS USEFUL AS MATRIX METALLOPROTEINASE INHIBITORS

(75) Inventors: Christopher Alan Conrad, Allegan, MI (US); Patrick Michael O'Brien, Stockbridge, MI (US); Daniel Fred Ortwine, Saline, MI (US); Joseph Armand Picard, Canton, MI (US); Drago Robert Sliskovic, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 74 days.

(21) Appl. No.: 10/049,544

(22) PCT Filed: Aug. 10, 2000

(86) PCT No.: PCT/US00/21884

§ 371 (c)(1),
(2), (4) Date: Feb. 13, 2002

(87) PCT Pub. No.: WO01/12592

PCT Pub. Date: Feb. 22, 2001

Related U.S. Application Data

(60) Provisional application No. 60/149,660, filed on Aug. 18, 1999.

(51) Int. Cl.[7] .................... C07D 307/91; C07D 407/12; A61K 31/343; A61K 31/351

(52) U.S. Cl. ....................... 514/320; 514/422; 514/432; 514/459; 514/468; 546/195; 548/531; 549/28; 549/414; 549/419

(58) Field of Search ................................ 514/320, 422, 514/432, 459, 468; 546/195; 548/531; 549/28, 414, 419

(56) References Cited

U.S. PATENT DOCUMENTS 6,143,744 A * 11/2000 Broka et al. ............. 514/238.2
6,376,506 B1 4/2002 Broka et al. ................ 514/292

FOREIGN PATENT DOCUMENTS

| | | |
|---|---|---|
| DE | 19802350 | 7/1998 |
| WO | 9907675 | 2/1999 |

OTHER PUBLICATIONS

Close, D.R., Ann. Rheum. Dis., 60, 2001, pp. 62–67, Medline abstract PMID 118.*
Jackson, C.et al, Inflamm. res., 50, 2001, 183–186.*
Greenwald, R.A., Ann N Y Acad Sci. 1999, vol. 878, pp. 413–419.*

* cited by examiner

*Primary Examiner*—Bruck Kifle
*Assistant Examiner*—Thomas McKenzie
(74) *Attorney, Agent, or Firm*—Claude P. Purchase, Jr.; Eric J. Baude

(57) ABSTRACT

Compounds of the formula;

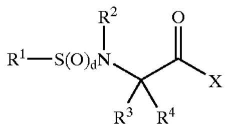

are useful for inhibiting matrix metalloproteinase enzymes in animals, and as such, prevent and treat diseases resulting from the breakdown of connective tissues. Also disclosed are methods for the preparation of such compounds, pharmaceutical compositions including the same, and methods of treating diseases in which matrix metalloproteinases are involved including multiple sclerosis, atherosclerotic plaque rupture, restenosis, aortic aneurysm, heart failure, periodontal disease, corneal ulceration, burns, decubital ulcers, chronic ulcers or wounds, cancer metastasis, tumor angiogenesis, osteoporosis, rheumatoid or osteoarthritis, renal disease, left ventricular dilation, or other autoimmune or inflammatory diseases dependent upon tissue invasion by leukocytes.

10 Claims, No Drawings

HYDROXAMIC ACID COMPOUNDS USEFUL AS MATRIX METALLOPROTEINASE INHIBITORS

CROSS-REFERENCE TO RELATED APPLICATIONS

This application claims benefit of priority from PCT International Patent Application Number PCT/US00/21884, filed Aug. 10, 2000, a §371 application of U.S. provisional application Ser. No. 60/149,660, filed Aug. 18, 1999.

FIELD OF THE INVENTION

This invention relates to a group of hydroxamic acid compounds and derivatives which inhibit matrix metalloproteinase enzymes and thus are useful for treating diseases resulting from tissue breakdown, such as heart disease, multiple sclerosis, arthritis, atherosclerosis, and osteoporosis.

BACKGROUND OF THE INVENTION

Matrix metalloproteinases (sometimes referred to as MMPs) are naturally occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues.

Stromelysin-1 and gelatinase A are members of the matrix metalloproteinases (MMP) family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., *Nature,* 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting metalloproteinase enzymes, thereby curtailing and/or eliminating the breakdown of connective tissues that results in the disease states.

The catalytic zinc in matrix metalloproteinases is typically the focal point for inhibitor design. The modification of substrates by introducing zinc chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of atherosclerotic plaques is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galla Z. S., Sukhova G. K., Lark M. W., and Libby P., "Increased expression of matrix metalloproteinases and matrix degrading activity in vulnerable regions of human atherosclerotic plaques," *J. Clin. Invest.,* 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization," *Proc. Nat'l. Acad. Sci.,* 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurysms and aortic stenosis (Vine N. and Powell J. T., "Metalloproteinases in degenerative aortic diseases," *Clin. Sci.,* 1991;81:233–239).

Heart failure arises from a variety of diverse etiologies, but a common characteristic is cardiac dilation which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure," *Am. J. Cardiol.,* 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha i.e., Voelker D. J., Campbell S. E., and Weber K. T., "Activated myocardial collagenase in idiopathic dilated cardiomyopathy," *Clin. Res.,* 1993;41:660A; Tyagi S. C., Reddy H. K., Voelker D., Tjara i.e., and Weber K. T., "Myocardial collagenase in failing human heart," *Clin. Res.,* 1993;41:681 A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction," *Can. J. Cardiol.,* 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure," *Am. J. Physiol.,* 1992;263:H266–H270).

Congestive heart failure (CHF) is a significant health care problem which currently accounts for 7% of total health care expenditures in the USA. Approximately 400,000 new cases of heart failure are identified annually. The primary cause for development of heart failure is ischemic heart disease, and most new cases occur after myocardial infarction. The number of hospital discharges for heart failure has increased from 377,000 in 1979 to 875,000 in 1993, and the number of deaths during the same period has risen 82.5%. The average mortality rate eight years following initial diagnosis is 85% for men and 65% for women.

The development of CHF begins as an injurious process to the myocardium that reduces cardiac function (especially contractile or pump function) either in a specific region(s) or throughout its entire extent (i.e., globally). Heart failure is said to exist whenever the myocardial injury is of sufficient severity to reduce the heart's capacity to pump an adequate output of blood to satisfy the body's tissue requirements either at rest or during exercise. The disease state of heart failure is not a static situation, but instead progressively worsens until death occurs either suddenly (e.g., by cardiac arrhythmia or embolism to the brain or lung) or gradually from pump failure per se. The progressive decline in heart function in patients with CHF is characterized by progressive enlargement of the ventricular chambers (i.e., ventricular dilatation) and thinning and fibrosis of the ventricular muscle. The progressive ventricular enlargement and accompanying histologic changes in the ventricular muscle are termed "remodeling," a process that involves changes in myocardiocyte structure as well as changes in the amount and composition of the surrounding interstitial connective tissue. An important constituent of the interstitial connective tissue is a matrix of fibrillar collagen, the "tissue scaffolding" that contributes to the maintenance of proper ventricular geometry and structural alignment of adjoining cardiomyocytes. The interstitial collagen matrix is subject to increased dissolution and repair during "remodeling" that leads to ventricular enlargement and progressive heart failure. The deterioration of the collagen matrix is effected by increased activity of matrix metalloproteinases, the inhibition of which is a new treatment for heart failure and ventricular dilatation. Ventricular dilatation, the severity of which is measured by the end-diastolic and end-systolic volumes, is a prognostic marker of the probability of subsequent morbidity and mortality. The larger the ventricular chamber dimensions, the greater the likelihood of subsequent morbid events. Not only is pump function impaired by remodeling and ventricular dilation, but the enlarged chambers are prone to formation of clots, which can lead to stroke or embolism to other major organs (e.g., kidney, legs, intestinal tract).

Standard treatment for heart failure utilizes diuretics to decrease fluid retention, angiotensin converting enzyme inhibitors (ACE-Is) to reduce cardiac workload on the failing heart via vasodilation, and in the final stages of failure the positive inotrope digitalis to maintain cardiac output. Although ACE-Is have the benefit of increasing longevity unlike diuretics or positive inotropes, the beneficial effect of ACE-Is is limited to delaying death by only about 18 months. Clinical trials with β-adrenergic blockers were recently conducted based on the hypothesis that reducing sympathetic drive would decrease the metabolic load on heart muscle cells. Unfortunately, this class of compounds was also found to not have a substantial effect on the progression of heart failure. The failure or limited success of previous heart failure therapies clearly shows that the controlling mechanism(s) mediating heart failure has not been targeted.

Drug development of the treatment of heart failure since the 1960s has focused on cardiac muscle cells. The goal has been to reduce the workload on the cells, improve blood flow to the cells, increase the contraction of the muscle, decrease the metabolic demand on cardiac myocytes, or some combination of these by various means. Focus on cardiac myocytes may have served to focus attention too far downstream. Overt heart failure may be caused by the breakdown of cardiac connective tissue. The breakdown in cardiac connective tissue proteins thus mediates cardiac dilation, one of the earliest characteristics of heart failure.

We have now discovered that compounds which inhibit MMPs that mediate the breakdown of connective tissues are useful for treating heart failure and associated ventricular dilatation.

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat," *Circulation Research,* 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation," *Circulation Research,* 1994;75:41–54).

Normal kidney function is dependent on the maintenance of tissues constructed from differentiated and highly specialized renal cells which are in a dynamic balance with their surrounding extracellular matrix (ECM) components (Davies M. et al., "Proteinases and glomerular matrix turnover," *Kidney Int.,* 1992;41:671–678). Effective glomerular filtration requires that a semi-permeable glomerular basement membrane (GBM) composed of collagens, fibronectin, enactin, laminin and proteoglycans is maintained. A structural equilibrium is achieved by balancing the continued deposition of ECM proteins with their degradation by specific metalloproteinases (MMP). These proteins are first secreted as proenzymes and are subsequently activated in the extracellular space. These proteinases are in turn subject to counter balancing regulation of their activity by naturally occurring inhibitors referred to as TIMPs (tissue inhibitors of metalloproteinases).

Deficiency or defects in any component of the filtration barrier may have catastrophic consequences for longer term renal function. For example, in hereditary nephritis of Alport's type, associated with mutations in genes encoding ECM proteins, defects in collagen assembly lead to progressive renal failure associated with splitting of the GBM and eventual glomerular and interstitial fibrosis. By contrast in inflammatory renal diseases such as glomerulonephritis, cellular proliferation of components of the glomerulus often precede obvious ultrastructural alteration of the ECM matrix. Cytokines and growth factors implicated in proliferative glomerulonephritis such as interleukin-1, tumor necrosis factor, and transforming growth factor beta can unregulate metalloproteinase expression in renal mesangial cells (Martin J. et al., "Enhancement of glomerular mesangial cell neutral proteinase secretion by macrophages: role of interleukin 1," *J. Immunol.,* 1986;137:525–529; Marti H. P. et al., "Homology cloning of rat 72 kDa type IV collagenase: Cytokine and second-messenger inducibility in mesangial cells," *Biochem. J.,* 1993;291:441–446; Marti H. P. et al., "Transforming growth factor-b stimulates glomerular mesangial cell synthesis of the 72 kDa type IV collagenase," *Am. J. Pathol.,* 1994;144:82–94). These metalloproteinases are believed to be intimately involved in the aberrant tissue remodeling and cell proliferation characteristic of renal diseases, such as, IgA nephropathy which can progress to through a process of gradual glomerular fibrosis and loss of functional GBM to end-stage renal disease. Metalloproteinase expression has already been well-characterized in experimental immune complex-mediated glomerulonephritis such as the anti-Thy 1.1 rat model (Bagchus W. M., Hoedemaeker P. J., Rozing J., Bakker W. W., "Glomerulonephritis induced by monoclonal anti-Thy 1.1 antibodies: A sequential histological and ultrastructural study in the rat," *Lab. Invest.,* 1986;55:680–687; Lovett D. H., Johnson R. J., Marti H. P., Martin J., Davies M., Couser W. G., "Structural characterization of the mesangial cell type IV collagenase and enhanced expression in a model of immune complex mediated glomerulonephritis," *Am. J. Pathol.,* 1992;141:85–98).

Unfortunately at present, there are very limited therapeutic strategies for modifying the course of progressive renal disease. Although many renal diseases have an inflammatory component, their responses to standard immunosuppressive regimes are unpredictable and potentially hazardous to individual patients. The secondary consequences of gradual nephron failure such as activation of the renin-angiotensin system, accompanied by individual nephron glomerular hyperfiltration and renal hypertension, may be effectively treated with ACE inhibitors or angiotensin II receptor antagonists; but at best, these compounds can only reduce the rate of GFR decline.

A novel strategy to treat at least some renal diseases has been suggested by recent observations of MMP behavior. A rat mesangial cell MMP has been cloned (MMP-2) which is regulated in a tissue specific manner, and in contrast to other cellular sources such as tumor cell lines, is induced by cytokines (Brown P. D., Levy A. T., Margulies I., Liotta L. A., Stetler-Stevenson W. G., "Independent expression and cellular processing of Mr 72,000 type IV collagenase and interstitial collagenase in human tumorigenic cell lines," *Cancer Res.,* 1990;50:6184–6191; Marti H. P. et al., "Homology cloning of rat 72 kDa type IV collagenase: Cytokine and second-messenger inducibility in mesangial cells," *Biochem. J.,* 1993;291:441–446). While MMP-2 can specifically degrade surrounding ECM, it also affects the phenotype of adjacent mesangial cells. Inhibition of MMP-2 by antisense oligonucleotides or transfection techniques can induce a reversion of the proliferative phenotype of cultured mesangial cells to a quiescent or non-proliferative phenotype mimicking the natural in vitro behavior of these cells (Kitamura M. et al., "Gene transfer of metalloproteinase transin induces aberrant behaviour of cultured mesangial cells," *Kidney Int.,* 1994;45:1580–1586; Turck J. et al., "Matrix metalloproteinase 2 (gelatinase A) regulates glomerular mesangial cell proliferation and differentiation," *J. Biol. Chem.,* 1996;271:15074–15083).

Collagenase and stromelysin activities have been demonstrated in fibroblasts isolated from inflamed gingiva (Uitto V. J., Applegren R., and Robinson P. J., "Collagenase and neutral metalloproteinase activity in extracts from inflamed human gingiva," *J. Periodontal Res.,* 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva," *J. Periodontal Res.,* 1987;22:81–88). Proteolytic degradation of extracellular matrix has been observed in corneal ulceration following alkali burns (Brown S. I., Weller C. A., and Wasserman H. E., "Collagenolytic activity of alkali burned corneas," *Arch. Opthalmol.,* 1969;81:370–373). Thiol-containing peptides inhibit the collagenase isolated from alkali-burned rabbit corneas (Burns F. R., Stack M. S., Gray R. D., and Paterson C. A., *Invest. Opththamol.,* 1989;30:1569–1575).

Stromelysin is produced by basal keratinocytes in a variety of chronic ulcers (Saarialho-Kere U. K., Ulpu K., Pentland A. P., Birkedal-Hansen H., Parks W. C., Welgus H. G., "Distinct populations of basal keratinocytes express stromelysin-1 and stromelysin-2 in chronic wounds," *J. Clin. Invest.,* 1994;94:79–88).

Stromelysin-1 mRNA and protein were detected in basal keratinocytes adjacent to but distal from the wound edge in what probably represents the sites of proliferating epidermis. Stromelysin-1 may thus prevent the epidermis from healing.

Davies et al. (*Cancer Res.,* 1993;53:2087–2091) reported that a peptide hyroxamate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.,* 1992;52:2353–2356), and the natural tissue inhibitor of metalloproteinase-2 (TIMP-2) also showed blockage of tumor cell invasion in in vitro models (DeClerck Y. A., Perez N., Shimada H., Boone T. C., Langley K. E., and Taylor S. M., *Cancer Res.,* 1992;52:701–708). Studies of human cancers have shown that gelatinase A is activated on the invasive tumor cell surface (Strongin A. Y., Marmer B. L., Grant G. A., and Goldberg G. I., *J. Biol Chem.,* 1993;268:14033–14039) and is retained there through interaction with a receptor-like molecule (Monsky W. L., Kelly T., Lin C. Y., Yeh Y., Stetler-Stevenson W. G., Mueller S. C., and Chen W. T., *Cancer Res.,* 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute,* 1995;87:293; and Benelli R., Adatia R., Ensoli B., Stetler-Stevenson W. G., Santi L., and Albini A., *Oncology Research,* 1994;6:251–257).

Several investigators have demonstrated consistent elevation of stromelysin and collagenase in synovial fluids from rheumatoid and osteoarthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury," *Arthritis Rheum.,* 1992;35:35–42; Zafarullal M., Pelletier J. P., Cloutier J. M., and Marcel-Pelletier J., "Elevated metalloproteinases and tissue inhibitor of metalloproteinase mRNA in human osteoarthritic synovia," *J. Rheumatol.,* 1993;20:693–697). TIMP-1 and TIMP-2 prevented the formation of collagen fragments, but not proteoglycan fragments, from the degradation of both the bovine nasal and pig articular cartilage models for arthritis, while a synthetic peptide hydroxamate could prevent the formation of both fragments (Andrews H. J., Plumpton T. A., Harper G. P., and Cawston T. E., Agents Actions, 1992;37:147–154; Ellis A. J., Curry V. A., Powell E. K., and Cawston T. E., *Biochem. Biophys. Res. Commun.,* 1994;201:94–101).

Gijbels et al. (*J. Clin. Invest.,* 1994;94:2177–2182) recently described a peptide hydroxamate, GM6001, that suppressed the development or reversed the clinical expression of experimental allergic encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M. and Madri J. A., "The Induction of 72-kD Gelatinase in T-Cells upon Adhesion to Endothelial Cells is VCAM-1 Dependent," *J. Cell Biology,* 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provided the basis for the belief that an inhibitor of stromelysin-1 and/or gelatinase A will treat diseases involving disruption of extracellular matrix resulting in inflammation due to lymphocytic infiltration, inappropriate migration of metastatic or activated cells, or loss of structural integrity necessary for organ function.

The need continues for low molecular weight molecules which can be economically prepared and yet are effective inhibitors of metalloproteinases. An object of the present invention is to provide such compounds, their pharmaceutical formulations, and a method for using them to treat diseases mediated by metalloproteinases.

SUMMARY OF THE INVENTION

The present invention provides matrix metalloproteinase inhibitors useful in treatment of diseases and conditions where inhibition of matrix metalloproteinase enzymes is considered beneficial.

The compounds of the invention are hydroxamic acid compounds having Formula I:

I

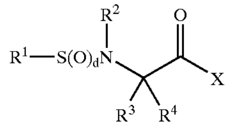

or a pharmaceutically acceptable salt thereof, wherein X is selected from OH and NHOH, and d is 1 or 2.

$R^1$ is selected from the group consisting of:

(a)

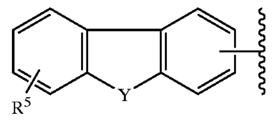

(b)

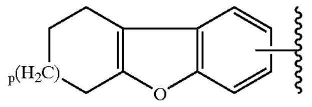

(c)

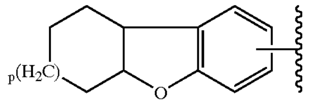

(d)

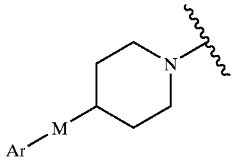

-continued (e)

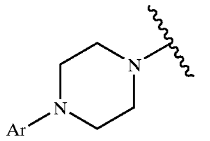

(f)

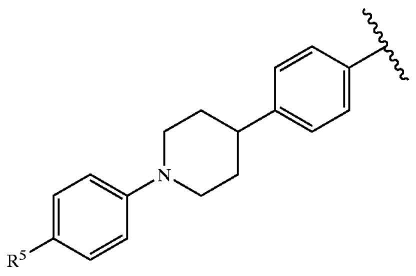

(g)

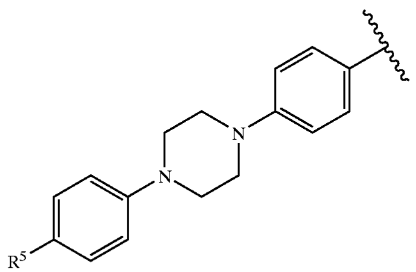

and (h)

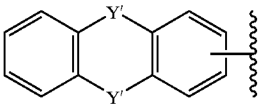

wherein Y is selected from the group consisting of O, S, $S(O)_d$ (where d is 1 or 2), $CH_2$, C(=O), and $NR^q$ (where $R^q$ is H, $C_{1-6}$ alkyl, or $C_{1-6}$ alkyl phenyl); each Y' is independently selected from the group consisting of O, S, $SO_2$, $CH_2$, C(=O), and NH; M is selected from the group consisting of O, S, and $CH_2$; $R^5$ is selected from the group consisting of H, $C_{1-10}$ alkyl, $CF_3$, $CONH_2$, halo, CN, COOH, $C_{1-4}$ alkoxy, CHO, $NO_2$, OH, $(CH_2)_pOH$, $(CH_2)_pNH_2$, Ar, and $NH_2$; p is from 0 to 3; and Ar is selected from the group consisting of (a) phenyl; (b) phenyl substituted with $C_{1-4}$ alkyl, $C_{1-4}$ alkoxy, halo, $NH_2$, $NO_2$, CN, COOH, $CONH_2$, $CF_3$, or $COOR^6$ (where $R^6$ is $C_{1-10}$ alkyl); and (c) heteroaryl.

$R^2$ is selected from the group consisting of (a) hydrogen; (b) $C_{1-4}$ alkyl; (c) benzyl; and (d) benzyl substituted with one or more of $C_{1-4}$ alkyl, $C_{1-4}$ alkoxy, F, Cl, Br, I, $NH_2$, $NO_2$, CN, carboxy, and $CO_2R^7$ (where $R^7$ is H or $C_{1-4}$ alkyl).

$R^3$ and $R^4$ are, independently, selected from the group consisting of $C_{1-20}$ alkyl (straight chain or branched); $C_{3-10}$ cycloalkyl; phenyl; phenyl substituted with $C_{1-4}$ alkyl, $C_{1-4}$ alkoxy, halo, $NH_2$, $NO_2$, CN, COOH, $CO_2R^7$ (wherein $R^7$ is as defined above), or $CF_3$; $C_{3-10}$ heterocyclic; and heteroaryl. $R^3$ and $R^4$ can be taken together to form a ring structure (incorporating the alpha carbon atom adjacent the carbonyl group in Formula I), as $-(CH_2)_s-$ bonded to the carbon atom adjacent the carbonyl group in Formula I, where s is an integer from 2 to 10. The ring optionally can further include one or more heteroatoms.

A further embodiment of the invention is a pharmaceutical formulation comprising a compound of Formula I admixed with a diluent, carrier, or excipient therefor.

The invention also provides methods for inhibiting the action of a matrix metalloproteinase enzyme in a mammal comprising administering a matrix metalloproteinase inhibiting amount of a compound of Formula I.

DETAILED DESCRIPTION OF THE INVENTION

The present invention is directed to compounds having Formula I:

I

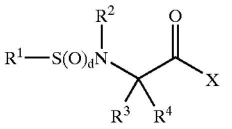

or a pharmaceutically acceptable salt thereof, wherein X is selected from OH and NHOH, and d is 1 or 2.

$R^1$ is selected from the group consisting of:

(a)

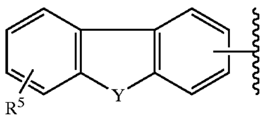

(b)

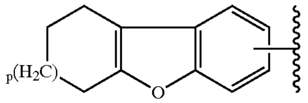

(c)

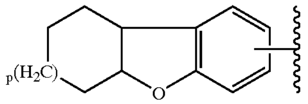

(d)

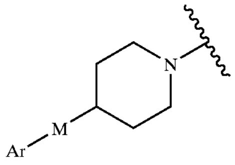

(e)

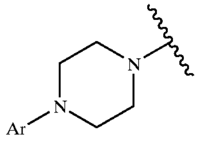

(f)

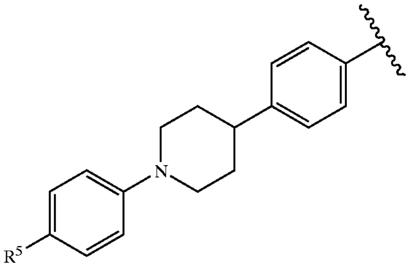

(g)

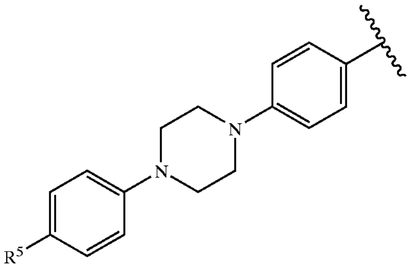

and

-continued (h)

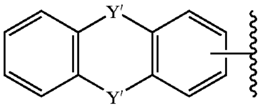

wherein Y and Y' are independently selected from the group consisting of O, S, $S(O)_d$ (where d is 1 or 2), $CH_2$, C(═O), and $NR^q$ (where $R^q$ is H, $C_{1-6}$ alkyl, or $C_{1-6}$ alkyl phenyl); each Y' is independently selected from the group consisting of O, S, $SO_2$, $CH_2$, C(═O), and NH; M is selected from the group consisting of O, S, and $CH_2$; $R^5$ is selected from the group consisting of H, $C_{1-10}$ alkyl, $CF_3$, $CONH_2$, halo, CN, COOH, $C_{1-4}$ alkoxy, CHO, $NO_2$, OH, $(CH_2)_pOH$, $(CH_2)_pNH_2$, Ar, and $NH_2$; p is from 0 to 3; and Ar is selected from the group consisting of (a) phenyl; (b) phenyl substituted with $C_{1-4}$ alkyl, $C_{1-4}$ alkoxy, halo, $NH_2$, $NO_2$, CN, COOH, $CONH_2$, $CF_3$, or $COOR^6$ (where $R^6$ is $C_{1-10}$ alkyl); and (c) heteroaryl, including, but not limited to, 2-, 3-, or 4-pyridyl, 2-, 4-, or 5- pyrimidinyl, 3- or 4-pyridazinyl, 2-pyrazinyl, 2- or 3-thienyl, 2- or 3-furanyl, 1-, 2-, 4-, or 5-imidazolyl, 1-, 3-, 4-, or 5-pyrazolyl, 1-, 2-, or 3-pyrrolyl, 2-, 4-, or 5-oxazolyl, 2-, 4-, or 5-thiazolyl, 3-, 4-, or 5-isoxazolyl, 2-, 3-, 4-, 5-, 6-, 7-, or 8-quinolinyl, or 3-, 4-, or 5-isothiazolyl.

Examples of $R^1$ groups include the following:

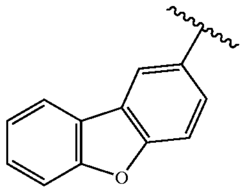

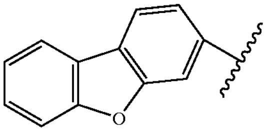

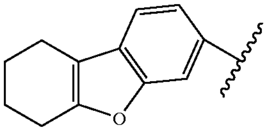

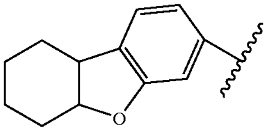

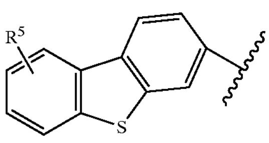

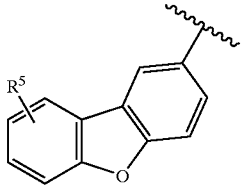

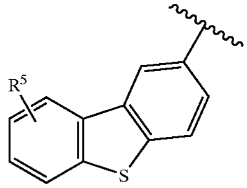

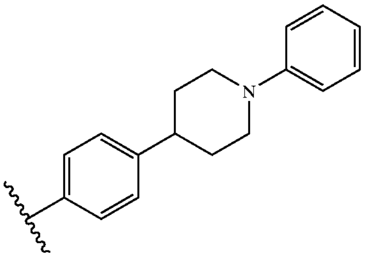

-continued

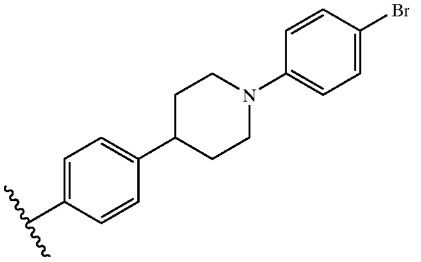

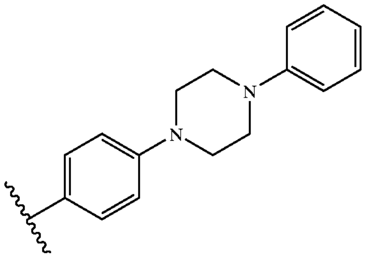

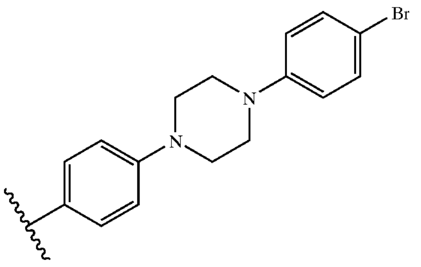

$R^2$ is selected from the group consisting of (a) hydrogen; (b) $C_{1-4}$ alkyl; (c) benzyl; and (d) benzyl substituted with one or more of $C_{1-4}$ alkyl, $C_{1-4}$ alkoxy, F, Cl, Br, I, $NH_2$, $NO_2$, CN, carboxy, and $CO_2R^7$ (where $R^7$ is H or $C_{1-4}$ alkyl).

$R^3$ and $R^4$ are, independently, selected from the group consisting of $C_{1-20}$ alkyl (straight chain or branched); $C_{3-10}$ cycloalkyl; phenyl; phenyl substituted with $C_{1-4}$ alkyl, $C_{1-4}$ alkoxy, halo, $NH_2$, $NO_2$, CN, COOH, $CO_2R^7$ (wherein $R^7$ is as defined above), or $CF_3$; $C_{3-10}$ heterocyclic; and heteroaryl. Also, $R^3$ and $R^4$ can be bonded or taken together to form a spiro cyclic ring (incorporating the alpha carbon atom adjacent the carbonyl group in Formula I), as $—(CH_2)_s—$ bonded to the carbon atom adjacent the carbonyl group in Formula I, where s is an integer from 2 to 10 (more preferably 3 to 9). The ring systems optionally can further include one or more heteroatoms.

For example, $R^3$ and $R^4$ can be taken together as $—(CH_2)_s—$ where s is from 2 to 10, to form a $C_{3-11}$ monocyclic ring, such as the following groups (wherein the terminal carbons are bonded to the alpha carbon atom adjacent the carbonyl group in Formula I): $—CH_2CH_2—$, $—CH_2CH_2CH_2—$, $—CH_2CH_2CH_2CH_2—$, $—CH_2CH_2CH_2CH_2CH_2—$, and $—CH_2CH_2CH_2CH_2CH_2CH_2—$ (forming 3-, 4-, 5-, 6-, and 7-membered rings, respectively).

$R^3$ and $R^4$ can be taken together to form one of the above-described spiro cyclic rings that additionally includes one or more heteroatoms (preferably 1 to 6 heteroatoms) at any location in the rings. The heteroatom is selected from the group consisting of O, S, and $NR^8$ (where $R^8$ is selected from H and $C_{1-3}$ alkyl).

Thus, $R^3$ and $R^4$ can also be taken together to form the empirical formula $—(CH_2)_sZ_g—$, wherein terminal carbons are bonded to the alpha carbon atom, s is an integer from 2 to 10, and g is an integer from 0 to 3. Each Z is a heteroatom located at any position of the group taken as $R^3$ and $R^4$, and each Z is independently selected from the group consisting of O, S, and $NR^8$ (where $R^8$ is selected from H and $C_{1-3}$ alkyl).

For example, a hetero-spiro cyclic ring may incorporate $—(CH_2)_aZ(CH_2)_b—$, where Z is the heteroatom (selected from the group consisting of O, S, and $NR^8$), a is from 1 to 10, and b is from 1 to 10, and the total of a and b is not more than 11, such as the following (where the terminal carbons are both bonded to the alpha carbon atom adjacent the carbonyl group in Formula I): $—CH_2OCH_2CH_2—$, $—CH_2CH_2OCH_2CH_2—$, $—CH_2CH_2OCH_2CH_2CH_2—$, $—CH_2N(H)CH_2CH_2—$, $—CH_2CH_2N(H)CH_2CH_2—$, $—CH_2CH_2N(H)CH_2CH_2CH_2—$, $—CH_2SCH_2CH_2—$, $—CH_2CH_2SCH_2CH_2—$, $—CH_2CH_2SCH_2CH_2CH_2—$, $—CH_2OCH_2CH_2OCH_2—$, $—CH_2N(H)CH_2CH_2N(H)CH_2—$, and $—CH_2SCH_2CH_2SCH_2—$. Thus, exemplary compounds of the invention can be represented by the following formula (where Z is the heteroatom and h is 0 or 1).

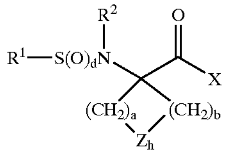

In preferred embodiments of compounds of Formula I, $R^1$ groups are selected from the following:

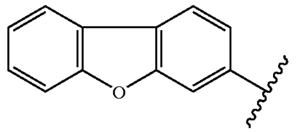

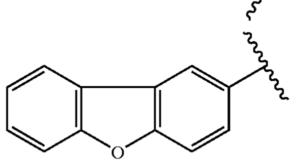

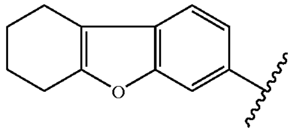

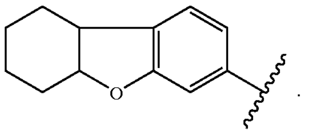

Preferably, d equals 2, $R^2$ is hydrogen, and X is NHOH or OH. $R^3$ and $R^4$ are preferably taken together to form a ringed structure, preferably selected from: $—CH_2CH_2CH_2CH_2—$ (where the terminal carbon atoms are bonded to the alpha carbon adjacent the carbonyl group in Formula I to form a cyclopentyl group); $—CH_2CH_2CH_2CH_2CH_2—$ (where the terminal carbon atoms are bonded to the alpha carbon adjacent the carbonyl group in Formula I to form a cyclohexyl group); and $—CH_2CH_2OCH_2CH_2—$ (where the terminal carbon atoms are bonded to the alpha carbon adjacent the carbonyl group in Formula I to form a 6-membered heterocyclic). In other preferred embodiments, $R^3$ and $R^4$ are each a methyl group.

In the formulas defining the compounds of the invention, halo refers to fluoro, chloro, bromo, and iodo, with chloro and bromo being preferred.

The term "$C_{1-4}$ alkyl" or "alkyl $C_{1-4}$" means straight and branched aliphatic groups having from 1 to 4 carbon atoms, examples of which include methyl, ethyl, n-propyl, isopropyl, n-butyl, sec-butyl, and tert-butyl. Thus, the term "$C_{1-20}$ alkyl" means straight and branched aliphatic groups having from 1 to 20 carbon atoms, and the term "$C_{1-10}$ alkyl" refers to straight and branched aliphatic groups having from 1 to 10 carbon atoms.

The term "alkoxy" means an alkyl group attached to an oxygen atom. Representative examples of alkoxy groups include methoxy, ethoxy, tert-butoxy, propoxy, and isobutoxy.

The term "aryl" means an aromatic hydrocarbon group. Representative examples of aryl groups include phenyl and naphthyl.

The term "cycloalkyl" means a cyclic aliphatic group. Examples of cycloalkyl groups include cyclopropyl, cyclobutyl, cyclopentyl, cyclohexyl, and cyclooctyl.

The symbol "—" means a bond.

The symbol:

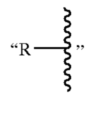

refers to a bonded R group.

A "heteroatom" is a nitrogen, oxygen, or sulfur atom.

The term "heteroaryl" means a mono- or bi-cyclic ring system containing 1 or 2 aromatic rings and containing at least 1 nitrogen, oxygen, or sulfur atom in an aromatic ring. Examples of heteroaryl groups include, but are not limited to, 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1-, 2-, 4-, or 5-imidazolyl, 1-, 3-, 4-, or 5-pyrazolyl, 2-, 4-, or 5-oxazolyl, 2-, 4-, or 5-thiazolyl, 3-, 4-, or 5-isoxazolyl, 3-, 4-, or 5-isothiazolyl, or 2-, 3-, 4-, 5-, 6-, or 7-indolyl. A heteroaryl can be substituted or unsubstituted, for example, with one or more, and in particular 1 to 3, substituents, such as halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl.

Thus, the MMP inhibiting compounds of the invention are derived from α, α'-disubstituted amino acids. The compounds where X equals NHOH are also referred to as hydroxamic acid compounds. The use of the zinc-binding hydroxamic acid moiety preferably provides compounds that inhibit all identified MMPs with superior (e.g., nanomolar range) potency over the corresponding carboxylic acids.

The compounds of the present invention can be therapeutically administered as the neat chemical, but it is preferable to administer compounds of Formula I as a pharmaceutical composition or formulation, as described below in further detail. Accordingly, the present invention further provides for pharmaceutical formulations comprising a compound of Formula I, together with one or more pharmaceutically acceptable carriers, and, optionally, other therapeutic and/or prophylactic ingredients. The carriers and other additives are "acceptable" in the sense of being compatible with the other ingredients of the formulation and not deleterious to the recipient thereof.

The term "pharmaceutically acceptable salts and prodrugs" refers to those salts (including carboxylate salts and amino acid addition salts) and prodrugs (including esters and amides) of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative anions include bromide, chloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulfonate, and the like. Cations include the alkali and alkaline earth metals, such as sodium, lithium, potassium, calcium, magnesium and the like, as well as nontoxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, Berge S. M. et al., "Pharmaceutical Salts," *J. Pharm. Sci.,* 1977;66:1–19, the disclosure of which is hereby incorporated herein by reference.

The term "prodrug" refers to compounds that are transformed in vitro, preferably rapidly, to yield the parent compound of the above formulae, for example, by hydrolysis in blood or other location. A thorough discussion is provided in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, the disclosures of both of which are hereby incorporated herein by reference.

Esters and amides can be used as prodrugs for the biologically active carboxylic acids of the present invention. Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to, benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

As appreciated by persons skilled in the art, reference herein to treatment extends to prophylaxis, as well as treatment of established diseases or symptoms. It is further appreciated that the amount of a compound of the invention required for use in treatment varies with the nature of the condition being treated, and with the age and condition of the patient and is ultimately determined by the attendant physician or veterinarian.

The pharmaceutical preparation is preferably in unit dosage form. The desired dose can be conveniently administered in a single dose, or as multiple doses administered at appropriate intervals, for example, as two, three, four, or more subdoses per day. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also the unit dosage form can be a capsule, tablet, cachet, or lozenge itself, or it can be the appropriate number of any of these in packaged form.

In therapeutic use as agents to inhibit a matrix metalloproteinase enzyme for the treatment of the conditions and diseases described herein, the compounds utilized in the pharmaceutical method of this invention are administered at a dose that is effective to inhibit the hydrolytic activity of one or more matrix metalloproteinase enzymes. The quantity of active component in a unit dose preparation may be varied or adjusted from about 0.1 to about 1000 mg, preferably about 10 to about 100 mg, according to the particular application and the potency of the active component.

An initial dosage of about 0.1 to about 500 mg per kilogram of body weight daily, for example about 1 to about 100 mg per kilogram of body weight daily, will generally be effective. A daily dose range of about 25 to about 75 mg per kilogram of body weight may be desirable. The dosages, however, may be varied depending upon the requirements of the patient, the severity of the condition being treated, and the compound being employed. Determination of the proper dosage for a particular situation is within the skill of the art. The composition can, if desired, also contain other compatible therapeutic agents.

Generally, treatment is initiated with smaller dosages which are less than the optimum dose of the compound. Thereafter, the dosage may be increased by small increments until the optimum effect under the circumstance is reached. For convenience, the total daily dosage may be divided and administered in portions during the day if desired. Typical dosages will be from about 0.1 to about 1000 mg per day, and more preferably about 25 to about 250 mg per day, such that an amount is provided that is effective to treat the particular disease being prevented or controlled. For a normal human adult having a body weight of about 70 kg, a dosage in the range of about 0.01 to about 100 mg per kilogram of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art. The term "patient" includes humans and animals.

The compounds and formulations of the present invention can be prepared and administered in a wide variety of oral and parenteral dosage forms. Thus, the compounds of the present invention can be administered by injection, that is intravenously, intramuscularly, intracutaneously, subcutaneously, intraduodenally, intra-arterially, intramuscularly, intra-articularly, and intraperitoneally, for example. Also, the compounds of the present invention can be administered by inhalation, for example, intranasally or deep lung inhalation. Additionally, the compounds of the present invention can be administered transdermally. The compounds of the invention can be administered transmucosally (e.g., sublingually or via buccal administration) or rectally. Ophthalmic formulations, eye ointments, powders, and solutions are also contemplated as being within the scope of this invention. Formulations of the invention are also described below in detail.

Those of skill in the art will understand that the following dosage forms may comprise as the active component, either a compound of the Formula I (including the preferred embodiments disclosed herein) or a corresponding pharmaceutically acceptable salt of a compound of Formula I.

The synthesis of exemplary sulfonamides of Formula I can be accomplished by the following preferred general schemes. Unless otherwise noted, all starting materials were obtained from commercial suppliers and used without further purification.

Scheme 1

A mixture of sodium phenoxide and a cycloalkeneoxide (where n is preferably 1 to 3) as shown below, are refluxed in water to form the hydroxy-ether compound of Formula II. The hydroxy-ether compound is oxidized to a ketone of Formula III using Jones Reagent or any other suitable oxidant.

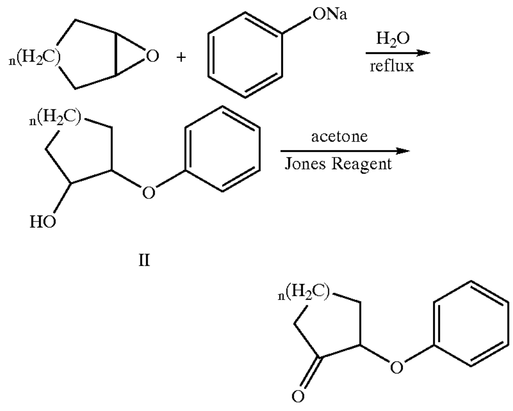

II

III

The ketone (III) is added to a mixture of sulfuric acid and phosphoric acid at 0° C. and allowed to warm to room temperature to form the compound of Formula IV.

IV

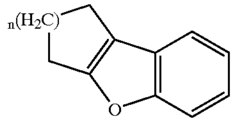

The compound of Formula IV is refluxed in an inert solvent such as 1,2-dichloroethane or dichloromethane with sulfur trioxide in dimethylformamide ($SO_3$.DMF) to form a sulfonic acid sodium salt of Formula V.

V

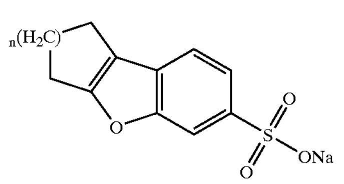

A sulfonyl chloride can be formed by refluxing the sodium salt of Formula V with an appropriate chlorinating agent such as thionyl chloride ($SOCl_2$), either neat or in an inert solvent such as toluene ($C_6H_5CH_3$) to produce the sulfonyl chloride of Formula VI.

VI

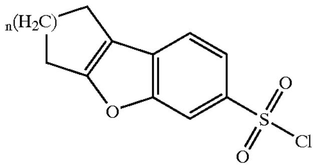

The sulfonyl chloride of Formula VI and a selected amino acid ester are coupled in an appropriate solvent such as aqueous tetraydrofuran or anhydrous tetrahydrofuran ("THF") with an acid scavenger such as triethylamine ("($NEt_3$)") , for example to produce the methyl ester of Formula VII.

VI +

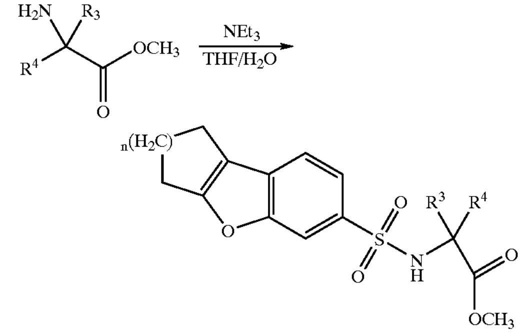

VII

From the methyl ester of Formula VII, a carboxylic acid of Formula VIII can be formed through base hydrolysis in aqueous tetrahydrofuran. The hydroxamic acid of Formula IX can be formed by first stirring the carboxylic acid with oxalyl chloride ($(COCl)_2$) or another suitable chlorinating agent in an inert solvent such as 1,2-dichloroethane or dichloromethane, to generate a carboxylic acid chloride which is then reacted with a solution of hydroxylamine to give the desired hydroxamic acid of Formula IX. The compounds of Formulas VIII and IX are preferred compounds of the invention, e.g., of Formula I.

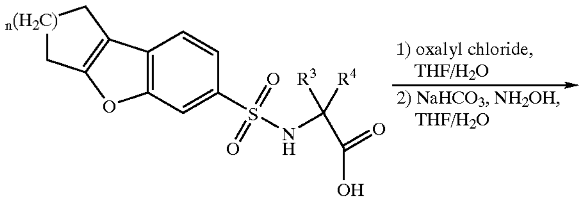

VIII

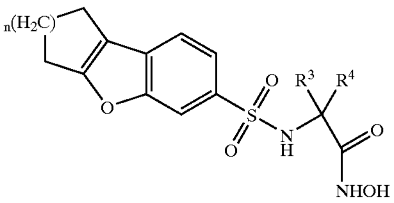

IX

Scheme 2

Another preferred scheme for producing preferred compounds of the invention is described below. A compound of the Formula X can be made by reduction of the sulfonic acid sodium salt of the Formula V (where n is preferably 1 to 3) from Scheme 1 in a solvent such as ethanol (EtOH) and aqueous tetrahydrofuran with palladium (20% Pd/C) or other suitable metal catalysts under hydrogen gas at elevated pressure. The sulfonyl chloride of the Formula XI can then be produced from the compound of Formula X by refluxing with an appropriate chlorinating agent such as phosphorus trichloride ($PCl_3$).

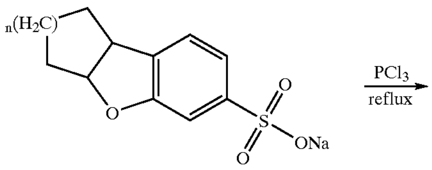

X

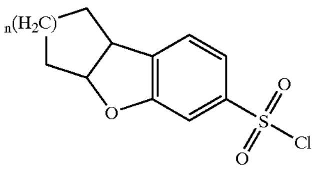

XI

The sulfonyl chloride of Formula XI is then combined with a selected amino acid ester in a solvent such as aqueous tetrahydrofuran or anhydrous tetrahydrofuran with an appropriate acid scavenger such as triethylamine ($NEt_3$) to form an N-sulfonamide amino acid ester, for example, the ester of Formula XII.

XI +

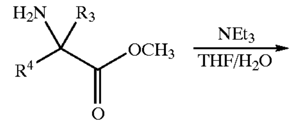

-continued

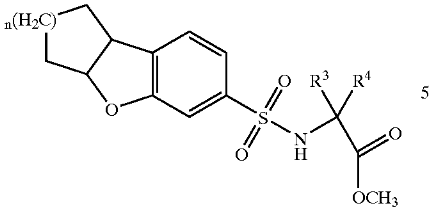

XII

Base hydrolysis of the ester of Formula XII forms the carboxylic acid of Formula XIII. A hydroxamic acid, for example the acid of Formula XIV, can then be formed by first stirring the carboxylic acid of Formula XIII with oxalyl chloride or other suitable chlorinating agent in an inert solvent such as 1,2-dichloroethane or dichloromethane, and then reacting the resultant carboxylic acid chloride with hydroxylamine.

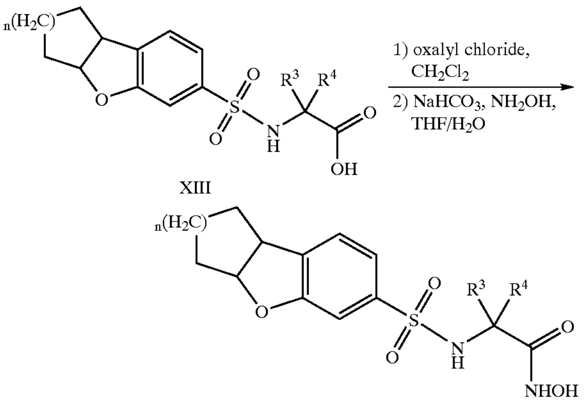

XIII

XIV

Preferred compounds of the invention can generally be prepared according to the synthetic schemes described herein. In each scheme, it is understood in the art that protecting groups can be employed where necessary in accordance with general principals of synthetic chemistry. Such protecting groups can be removed in the final steps of the synthesis under basic, acidic, or hydrogenolytic conditions which are readily apparent to those skilled in the art. By employing appropriate manipulation and protection of any chemical functionalities, synthesis of compounds of the invention not specifically set forth herein can be accomplished by methods analogous to the schemes set forth herein.

The present invention includes all possible stereoisomers and geometric isomers of compounds of Formula I, and includes not only racemic compounds but also the optically active isomers as well, for example where the substituents $R^3$ and $R^4$ differ. When a compound of Formula I is desired as a single enantiomer, it can be obtained either by resolution of the final product or by stereospecific synthesis from either isomerically pure starting material or any conventional intermediate. Resolution of the final product, an intermediate, or a starting material can be achieved by any suitable method known in the art. Additionally, in situations where tautomers of the compounds in Formula I are possible, the present invention is intended to include all tautomeric forms of the compounds.

The synthesis of typical sulfonamides of Formula I is illustrated by the following examples. The examples are representative only, and are not intended to be limiting in any respect. The ratios disclosed herein are volume ratios unless otherwise noted.

EXAMPLES 1 AND 2

Synthesis of 1-(4'-Bromo-biphenyl-4-sulfonylamino)-cyclopentanecarboxylic acid Step (a)

A mixture of 4'-bromobenzene-4-sulfonyl chloride (2.5 g, 7.5 mmol) and methyl 1-amino-1-cyclopentanecarboxylate (1.4 g, 7.9 mmol) was diluted with aqueous tetrahydrofuran (1:1, 40 mL), then treated dropwise with triethylamine (1.5 g, 14.8 mmol). The resulting reaction mixture was stirred at room temperature for 4 hours, followed by the addition of aqueous HCl (1 M, 20 mL) and ethyl acetate (50 mL). The reaction mixture was allowed to separate into an aqueous phase and an organic phase. The organic phase was separated from the aqueous phase, dried (over $MgSO_4$), and concentrated. The resulting residue was triturated with diethyl ether, and the solid was collected by filtration to give the sulfonamide methyl ester (2.5 g, 76%) as a white solid. The melting point of this compound was determined to be 148–150° C. $^1$HNMR ($CDCl_3$): δ7.9 (d, 2H), 7.7 (d, 2H), 7.6 (d, 2H), 7.5 (d, 2H), 3.6 (s, 3H), 2.1–1.9 (m, 4H), 1.7 (m, 4H) ppm.

Step (b)

The ester prepared in Step (a) (2 g, 4.6 mmol) was suspended in aqueous methanol (5:1, 30 mL), then treated with solid sodium hydroxide (0.38 g, 9.5 mmol) in one portion. The reaction mixture was refluxed overnight, cooled, and the methanol was concentrated in vacuo. The aqueous suspension was diluted with water (50 mL), acidified (to a pH of 1), and the resulting precipitate was collected by filtration and oven dried (40° C.) to a constant weight. The crude product was recrystallized from ethyl acetate/ethanol to give 1-(4'-bromo-biphenyl-4-sulfonylamino)-cyclopentanecarboxylic acid (Example 1) (1.2 g, 62%) as a white solid. The melting point of this compound was determined to be 229–231° C. $^1$HNMR (DMSO-$d_6$): δ8.1 (s, 1H), 7.8 (s, 4H), 7.7 (s, 4H), 1.9 (m, 4H), 1.5–1.3 (m, 4H) ppm. This compound has the structure shown below:

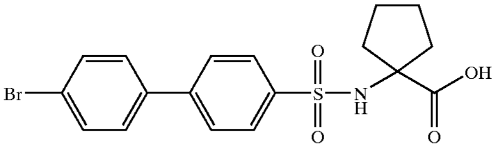

Synthesis of 1-(4'-Bromo-biphenyl-4-sulfonylamino)-cyclopentanecarboxylic Acid Hydroxamide Step (c)

The acid prepared in Step (b) (0.35 g, 0.82 mmol) was suspended in dichloromethane (5 mL) and treated with oxalyl chloride (0.31 g, 2.5 mmol) in one portion. DMF was added as a catalyst, and the reaction mixture was stirred for 6 hours at room temperature. The solvent was concentrated in vacuo and the resulting residue was suspended in hexane and concentrated to dryness. The crude product was triturated with hexane and collected by filtration to yield the acid chloride (0.34 g, 94%) as a pale yellow solid. $^1$HNMR ($CDCl_3$): δ7.9 (d, 2H), 7.7 (d, 2H), 7.6 (d, 2H), 7.5 (d, 2H), 5.4 (s, 1H), 2.2 (m, 2H), 1.9 (m, 2H), 1.7 (m, 4H) ppm.

Step (d)

To a THF solution of acid chloride (0.33 g, 0.74 mmol), cooled to 0° C., were added hydroxylamine hydrochloride (0.10 g, 1.5 mmol) and aqueous sodium carbonate (0.18 g, 2.2 mmol in 1.5 mL $H_2O$). The reaction mixture then was allowed to warm to room temperature and was stirred overnight. The reaction mixture then was diluted with aqueous HCl (1 M, 10 mL) and ethyl acetate (20 mL). The reaction mixture was allowed to separate into an aqueous phase and an organic phase. The organic phase was separated from the aqueous phase, dried (over $MgSO_4$), and concentrated to dryness. The resulting residue was triturated with hexane/ethyl acetate (1:1) and collected by filtration. The solid was recrystallized from ethyl acetate/ethanol to yield 1-(4'-bromo-biphenyl-4-sulfonylamino)-cyclopentanecarboxylic acid hydroxyamide (Example 2) (0.18 g, 56%) as a white solid. During a melting point determination, the compound decomposed at 184–185° C. $^1$HNMR (DMSO-$d_6$): δ8.7 (s, 1H), 7.9 (s, 1H), 7.85 (s, 4H), 7.7 (s, 4H), 1.8 (m, 4H), 1.4 (m, 2H), 1.2 (m, 2H) ppm. This compound has the structure shown below.

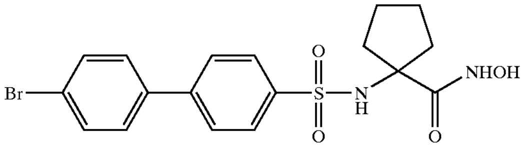

Using the procedure described for Example 2 made possible the synthesis of the additional hydroxamic acids of Examples 3 and 4.

EXAMPLE 3

1-(4'-Bromo-biphenyl-4-sulfonylamino)-cyclohexanecarboxylic acid hydroxyamide

During a melting point determination, the compound decomposed at 207–208° C. $^1$HNMR (DMSO-$d_6$): δ8.6 (s, 1H), 7.9 (s, 4H), 7.7 (s, 4H), 7.65, (s, 1H), 1.8–1.6 (m, 4H), 1.3–1.1 (m, 6H) ppm.

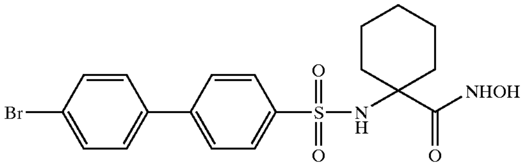

EXAMPLE 4

2-(4'-Bromo-biphenyl-4-sulfonylamino)-N-hydroxy-2-methyl-propionamide (PD 0213521)

During a melting point determination, the compound decomposed at 173–174° C. $^1$HNMR (DMSO-$d_6$): δ8.7 (s, 1H), 7.9–7.8 (m, 5H), 7.7 (s, 4H), 1.2 (s, 6H) ppm.

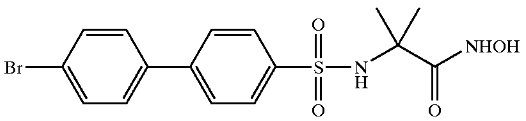

Using the procedure described for Example 2 also made possible the synthesis of the corresponding carboxylic acids (Examples 5 and 6).

EXAMPLE 5

1-(4'-Bromo-biphenyl-4-sulfonylamino)-cyclohexanecarboxylic acid

The melting point of this compound was determined to be 235–237° C. $^1$HNMR (DMSO-$d_6$): δ7.9 (s, 1H), 7.8 (s, 4H), 7.7 (s, 4H), 1.8–1.6 (m, 4H), 1.3–1.1 (m, 6H) ppm.

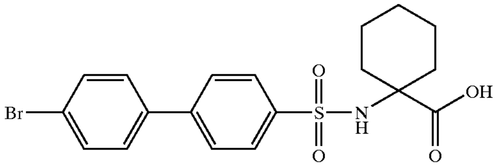

EXAMPLE 6

2-(4'-Bromo-biphenyl-4-sulfonylamino)-2-methyl-propionic acid

The melting point of this compound was determined to be 185–187° C. $^1$HNMR (DMSO-$d_6$): δ8.1 (s, 1H), 7.9 (s, 4H), 7.7 (s, 4H), 1.3 (s, 6H) ppm.

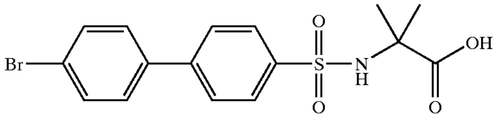

EXAMPLES 7 AND 8

Synthesis of 2-methyl-2-(6,7,8,9-tetrahydro-dibenzofuran-3-sulfonylamino)-propionic acid Step (a)

Cyclohexene oxide (10 g, 0.102 mol) was added dropwise to an aqueous solution of sodium phenoxide trihydrate (31.6 g, 0.186 mol; 250 mL). The mixture was refluxed overnight, cooled to room temperature, and a precipitate was collected by filtration. The precipitate was dissolved in ethyl acetate. The organic phase was washed with 1 M NaOH, brine, dried (over $MgSO_4$), and concentrated to give solid 2-phenoxy-cyclohexanol (a compound of general Formula II) (13.84 g, 70%). The melting point of this compound was determined to be 79–80° C. $^1$HNMR ($CDCl_3$ ): δ7.3 (m, 2H), 6.9 (m, 3H), 4.0 (m, 1H), 3.7 (m, 1H), 2.1 (m, 2H), 1.8 (m, 4H), 1.4 (m, 4H) ppm.

Step (b)

2-Phenoxy-cyclohexanol (13.64 g, 0.071 mol) was dissolved in acetone (260 mL), cooled to between 0° C. to 5° C., and Jones Reagent (2 M, 78 mL) was added dropwise. The reaction was stirred for 4.5 hours. The reaction mixture was poured into water (250 mL), and diethyl ether (500 mL) was added. The organic phase was separated from the aqueous phase, then washed with water, dried (over $MgSO_4$), and concentrated to yellow crystals. The crystals were recrystallized from pentane to give 2-phenoxy-cyclohexanone (a compound of general Formula III) (10.22 g, 76%). $^1$ HNMR ($CDCl_3$): δ7.2 (m, 2H), 7.0 (m, 2H), 6.8 (d, 1H), 4.6 (m, 1H), 2.6 (m, 1H), 2.4 (m, 2H), 2.0–1.8 (m, 5H) ppm.

Step (c)

2-Phenoxy-cyclohexanone (10.2 g, 0.054 mol) was ad ded slowly to a cooled mixture of phosphoric acid and sulfuric acid (3:1, 80 mL) at 0° C. The reaction was stirred for 4 hours and then was poured over ice. Diethyl ether (300 mL) was added. The organic phase was separated from the aqueous phase, then washed with water, sodium bicarbonate, and water, dried (over $MgSO_4$), and concentrated to a viscous liquid. The crude product was dissolved in hexane and purified by silica gel column chromatography to give 2,3,4-tetrahydro-dibenzofuran (a compound of general Formula IV) (5.72 g, 61%). $^1$HNMR ($CDCl_3$): δ7.4 (m, 2H), 7.2 (m, 2H), 2.7 (m, 4H), 1.9 (m, 4H) ppm.

Step (d)

1,2,3,4-Tetrahydro-dibenzofuran (5.7 g, 0.033 mol) was added dropwise to $SO_3$.DMF complex (16.3 g) suspended in 1,2-dichloroethane (100 mL). The reaction was refluxed overnight. The reaction mixture was then cooled, concentrated to a thick liquid, taken up in water (300 mL, and basified with 1 M NaOH (260 mL, pH 12). Crystallization occurred on an ice bath and crystals were collected by filtration. The crystals were slurried in tetrahydrofuran and collected by filtration. The product was dried to give 1,2,3,4-tetrahydro-dibenzofuran-3-sulfonic acid sodium salt (a compound of general Formula V) (4.30 g, 47%). $^1$HNMR (DMSO): δ7.6 (s, 1H), 7.4 (m, 2H), 2.6 (m, 4H), 1.9 (m, 4H) ppm.

Step (e)

The compound produced in Step (d) above (2 g, 7.24 mmol) was suspended in toluene (25 mL), then thionyl chloride (3.45 g, 28.96 mmol) was added dropwise. N,N-dimethylformamide (2 drops) was added, and the reaction was refluxed for 3 hours, cooled to room temperature, then stirred for 3 days. The reaction mixture was concentrated and triturated twice with hexane and reduced. The crude crystals were triturated with a mixture of 10% ethyl acetate:hexane, then collected by filtration. The filtrate was concentrated and washed with hexane to yield a second crop. The crystals were dried to provide a sulfonyl chloride (a compound of general Formula VI) (1.2 g, 61%). $^1$HNMR ($CDCl_3$): δ8.1 (s, 1H), 7.9 (d, 1H), 7.6 (d, 1H), 2.8 (m, 4H), 1.9 (m, 4H) ppm.

Step (f)

A mixture of the sulfonyl chloride compound prepared in Step (e) (1 g, 3.69 mmol) and α-amino isobutyric acid methyl ester hydrochloride (624 mg, 4.06 mmol) was diluted with aqueous tetrahydrofuran (4:1, 40 mL) and treated dropwise with triethylamine (785 mg, 7.75 mmol). The reaction mixture was stirred at room temperature for 20 hours followed by the addition of aqueous hydrochloric acid (1 M, 20 mL) and ethyl acetate (50 mL). The organic phase was separated from the aqueous phase, dried (over MgSO4), and concentrated. The resulting crystals were triturated with 4:1 hexane:ethyl acetate and collected by filtration to give 2-methyl-2-(6,7,8,9-tetrahydro-dibenzofuran-3-sulfonylamino)-propionic acid methyl ester (a compound of general Formula VII) (586 mg, 25%) as a white solid. $^1$HNMR ($CDCl_3$): δ7.9 (s, 1H), 7.7 (d, 1H), 7.4 (d, 1H), 3.6 (s, 3H), 2.8 (m, 2H), 2.6 (m, 2H), 1.9 (m, 4H), 1.4 (s, 6H) ppm.

Step (g)

The 2-methyl-2-(6,7,8,9-tetrahydro-dibenzofuran-3-sulfonylamino)-propionic acid methyl ester (586 mg, 1.67 mmol) was suspended in aqueous tetrahydrofuran (1:1, 22 mL) and treated with aqueous sodium hydroxide (1 M, 7 mL). The reaction mixture was stirred at room temperature for 3 days. The tetrahydrofuran was concentrated in vacuo. The aqueous suspension was diluted with water (40 mL) and washed with diethyl ether. The aqueous phase was separated from the organic phase, and acidified (to a pH of 1). The resulting precipitate was collected by filtration and oven dried to give 2-methyl-2-(6,7,8,9-tetrahydro-dibenzofuran-3-sulfonylamino)-propionic acid (a compound of general Formula VIII) (457 mg, 81%), the structure of which is shown below. The melting point of this compound was determined to be 237–240° C. $^1$HNMR (DMSO-$d_6$): δ8.0 (s, 1H), 7.8 (s, 1H), 7.6 (m, 2H), 2.7(m, 2H), 2.6 (m, 2H), 1.8 (m, 4H), 1.1 (s, 6H) ppm.

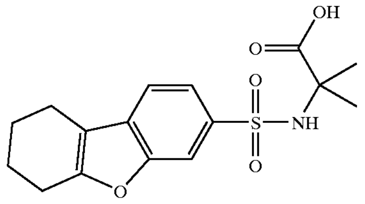

Synthesis of N-Hydroxy-2-methyl-2-(6,7,8,9-tetrahydro-dibenzofuran-3-sulfonylamino)-propionamide Step (h)

2-Methyl-2-(6,7,8,9-tetrahydro-dibenzofuran-3-sulfonylamino)-propionic acid (387 mg, 1.15 mmol) was suspended in 1,2-dichloroethane (22 mL), then oxalyl chloride (438 mg, 3.45 mmol) was added dropwise. N,N-dimethylformamide (2 drops) was added and a gas evolved from the solution. The reaction was stirred until the solids were dissolved. The reaction mixture was concentrated by evaporation, washed with hexane, concentrated again, and dissolved in tetrahydrofuran (20 mL), then added to an aqueous tetrahydrofuran solution (1:1, 34 mL, 5° C.) of hydroxylamine hydrochloride (800 mg, 11.5 mmol) and sodium bicarbonate (1.8 g, 17.25 mmol). The reaction was stirred, warming up to room temperature, overnight. The tetrahydrofuran was removed from the reaction mixture in vacuo. To the residue, 1 M HCl and dichloromethane were added. The organic phase was separated from the organic phase, dried (over $MgSO_4$), and concentrated. The crystals were rinsed with ethyl acetate, then collected by filtration to give N-hydroxy-2-methyl-2-(6,7,8,9-tetrahydro-dibenzofuran-3-sulfonylamino)-propionamide (a compound of general Formula IX) (235 mg, 58%), the structure of which is shown below. The melting point of this compound was determined to be 175–176° C. $^1$HNMR ($CDCl_3$): δ10.0 (s, 1H), 7.6 (s, 1H), 7.4 (d, 1H), 7.2 (m, 2H), 2.6 (m, 2H), 2.4 (m, 2H) 1.6 (m, 4H), 1.0 (s, 6H) ppm.

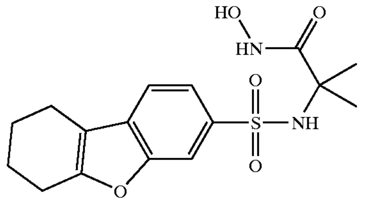

Using the procedure described for Example 7 made possible the synthesis of Examples 9 and 10.

EXAMPLE 9

1-(6,7,8,9-Tetrahydro-dibenzofuran-3-sulfonylamino)-cyclopentane carboxylic acid MS-APCI (negative ion mode) m/z=362.1 (M–H).

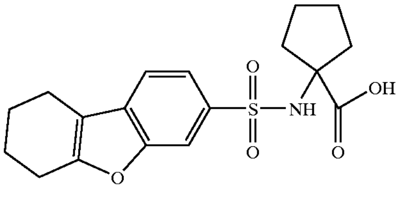

EXAMPLE 10

2-(5,6,7,8,9,9a-Hexahydro-4bH-10-oxa-benzo[a]azulene-2-sulfonylamino)-2-methyl-propionic acid The melting point of this compound was determined to be >200° C. $^1$HNMR (DMSO): δ7.9 (s, 1H), 7.8 (s, 1H), 7.6 (s, 2H), 2.9 (m, 2H), 2.7 (m, 2H), 1.8 (m, 6H) ppm.

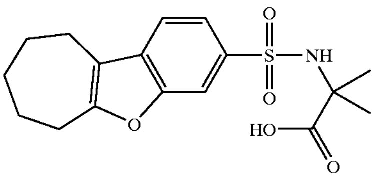

EXAMPLE 11

Using the procedure described for Example 8 made possible the synthesis of Example 11, N-hydroxy-2-methyl-2-(6,7,8,9-tetrahydro-5H-10-oxa-benzo[a]azulene-2-sulfonylamino)-propionamide. The melting point of this compound was determined to be 167–171 ° C. $^1$H NMR ($CDCl_3$): δ7.6 (s, 1H), 7.3 (m, 1H), 7.1 (m, 1H), 6.9 (s, 1H), 2.6 (m, 2H), 2.4 (m, 2H), 1.5 (m, 6H) ppm.

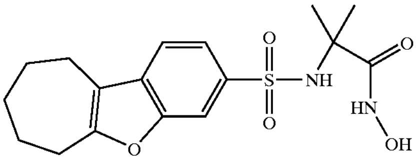

Additional compounds that can be made with the procedure for Examples 7 and 8 are the following:

EXAMPLE 12

2-(2,3-Dihydro-1H-8-oxa-cyclopenta[a]indene-6-sulfonylamino)-2-methyl-propionic acid

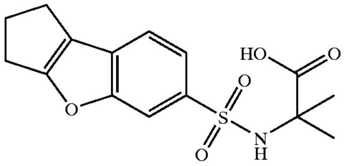

EXAMPLE 13

2-(2,3-Dihydro-1H-8-oxa-cyclopenta[a]indene-6-sulfonylamino)-N-hydroxy-2-methyl-propionamide

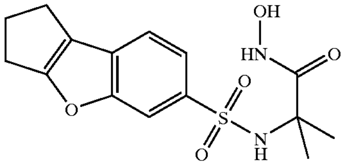

EXAMPLE 14

1-(2,3-Dihydro-1H-8-oxa-cyclopenta[a]indene-6-sulfonylamino)-cyclopentane carboxylic acid

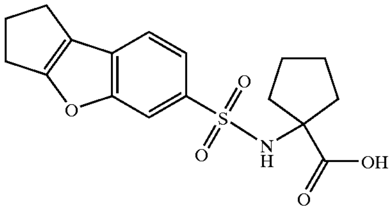

EXAMPLE 15

1-(2,3-Dihydro-1H-8-oxa-cyclopenta[a]indene-6-sulfonylamino)-cyclopentane carboxylic acid hydroxyamide

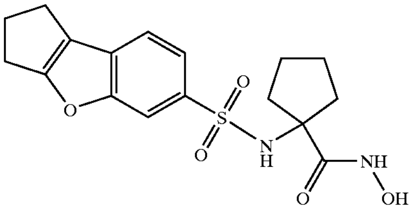

EXAMPLE 16

1-(6,7,8,9-Tetrahydro-dibenzofuran-3-sulfonylamino)-cyclopentane carboxylic acid hydroxyamide

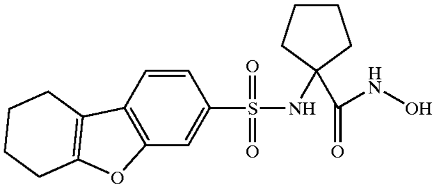

EXAMPLE 17

1-(6,7,8,9-Tetrahydro-5H-10-oxa-benzo[a]azulene-2-sulfonylamino)-cyclopentane carboxylic acid

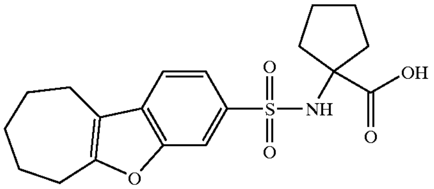

EXAMPLE 18

1-(6,7,8,9-Tetrahydro-5H-10-oxa-benzo[a]azulene-2-sulfonylamino)-cyclopentane carboxylic acid hydroxyamide

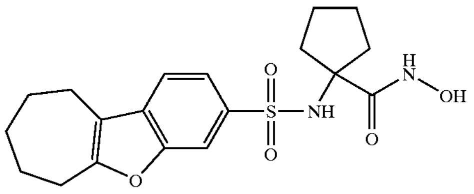

EXAMPLE 19

2-(5,6,7,8,9,10-Hexahydro-11-oxa-cycloocta[a]indene-2-sulfonylamino)-2-methyl-propionic acid

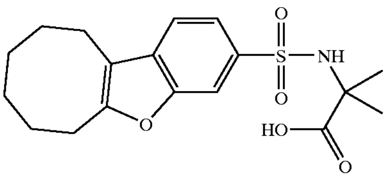

EXAMPLE 20

2-(5,6,7,8,9,10-Hexahydro-11-oxa-cycloocta[a]indene-2-sulfonylamino)-N-hydroxy-2-methyl-propionamide

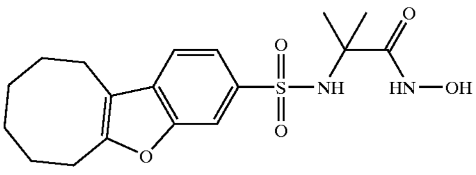

EXAMPLE 21

1-(5,6,7,8,9,10-Hexahydro-11-oxa-cycloocta[a]indene-2-sulfonylamino)-cyclopentane carboxylic acid

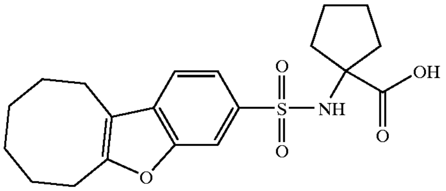

EXAMPLE 22

1-(5,6,7,8,9,10-Hexahydro-11-oxa-cycloocta[a]indene-2-sulfonylamino)-cyclopentane carboxylic acid hydroxyamide

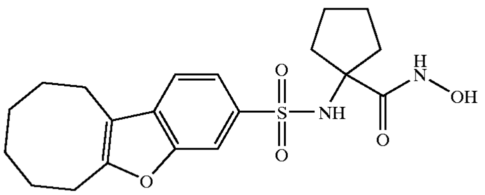

EXAMPLE 23

Synthesis of 2-(5a,6,7,8,9,9a-Hexahydro-dibenzofuran-3-sulfonylamino)-2-methyl-propionic acid Step (a)

1,2,3,4-Tetrahydro-dibenzofuran-3-sulfonic acid sodium salt (a compound of general Formula V) (2.24 g, 8.17 mmol) was dissolved in ethanol (50 mL), water (50 mL). To this solution, 20% Pd/C (0.2 g) was added as a catalyst, and the resulting mixture was pressurized (49.6 psi) under hydrogen. The reaction was allowed to shake for 11 hours. The Pd/C catalyst was filtered off, and the filtrate was concentrated to give a white solid (a compound of general Formula X) (1.95 g, 86%). $^1$HNMR (DMSO): δ7.1 (s, 2H), 6.9 (s, 1H), 4.6 (m, 1H), 3.2 (m, 1H), 1.8 (m, 4H), 1.3 (m, 4H) ppm.

Step (b)

The sulfonic acid sodium salt produced in Step (a) (894 mg, 3.24 mmol) was slowly added to phosphorus trichloride (12 mL), then refluxed for 5 days. The reaction mixture was poured over ice (300 mL) to which diethyl ether (300 mL) was added. The organic phase was separated from the aqueous phase, then washed with brine, dried (over $MgSO_4$), and concentrated to give the sulfonyl chloride (a compound of general Formula XI), a viscous liquid (591 mg, 67%). $^1$HNMR ($CDCl_3$): δ7.6 (m, 1H), 7.3 (m, 2H), 4.8 (m, 1H), 3.3 (m, 1H), 1.9 (m, 4H), 1.5 (m, 4H) ppm.

Step (c)

Triethylamine (769 mg, 7.60 mmol) was added dropwise to a suspension of α-amino isobutyric acid (500 mg, 3.26 mmol) in dichloromethane (20 mL). The sulfonyl chloride (591 mg, 2.17 mmol) prepared in the previous step was taken up in dichloromethane (5 mL) and added to the amino acid solution. The reaction was stirred at room temperature for 20 hours. The reaction was concentrated, and the residue was dissolved in ethyl acetate, washed with hydrochloric acid (1 M), dried (over $MgSO_4$), and concentrated to give 2-(5a,6,7,8,9,9a-hexahydro-dibenzofuran-3-sulfonylamino)-2-methyl-propionic acid methyl ester (a compound of general Formula XII) as a viscous orange liquid (420 mg, 55%). $^1$HNMR ($CDCl_3$): δ7.4 (m, 1H), 7.2 (m, 3H), 4.7 (m, 1H), 3.6 (s, 3H), 3.2 (m, 1H), 1.9 (m, 4H), 1.5 (m, 4H), 1.4 (s, 6H) ppm.

Step (d)

Sodium hydroxide (1 M, 6 mL) was added to a solution of the methyl ester prepared in Step (c) (420 mg, 1.19 mmol) in aqueous tetrahydrofuran (1:1, 10 mL). The reaction was stirred at room temperature for 20 hours. The tetrahydrofuran was removed under vacuum, and the concentrated solution was acidified with concentrated hydrochloric acid to pH 1. The crystals that formed were collected by filtration and dried in a vacuum oven to yield 2-(5a,6,7,8,9,9a-hexahydrodibenzofuran-3-sulfonylamino)-2-methyl-propionic acid (a compound of general Formula XIII) (297 mg, 73%), the structure of which is shown below. The melting point of this compound was determined to be 154–165° C. $^1$HNMR (DMSO-$d_6$): δ7.9 (s, 1H), 7.3 (m, 3H), 7.1 (s, 1H), 4.7 (m, 1H), 2.4 (s, 6H), 1.8 (m, 4H), 1.3 (m, 4H) ppm.

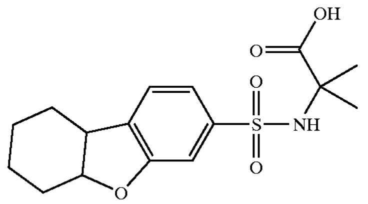

EXAMPLE 24

Synthesis of 2-(5a,6,7,8,9,9a-Hexahydro-dibenzofuran-3-sulfonylamino)-N-hydroxy-2-methyl-propionamide The compound of Example 23 (267 mg, 0.79 mmol) was suspended in dichloromethane (13 mL), followed by the addition of oxalyl chloride (301 mg, 2.37 mmol). One drop of DMF was added and a gas was emitted from the reaction. The reaction mixture was stirred at room temperature until dissolution occurred. The reaction was concentrated, washed with hexane, and concentrated to dryness. This crude compound was dissolved in tetrahydrofuran (6 mL), then added to hydroxylamine hydrochloride (550 mg, 7.90 mmol) and sodium bicarbonate dissolved in cold aqueous tetrahydrofuran (1:1, 10 mL). The resulting mixture was stirred for 15 hours. The tetrahydrofuran was removed from the solution under vacuum, then the reaction mixture was washed with hydrochloric acid (1 M) and dichloromethane. The organic phase was separated from the aqueous phase, concentrated and the residue was washed with hexane, concentrated again, and washed with ethyl acetate. The product was recrystallized overnight from ethyl acetate. The solid was collected by filtration and dried in a vacuum oven at 40° C. to yield 2-(5a,6,7,8,9,9a-hexahydro-dibenzofuran-3-sulfonylamino)-N-hydroxy-2-methyl-propionamide (a compound of general Formula XIV), the structure of which is shown below. The melting point of this compound was determined to be 153° C. to 159° C. $^1$HNMR ($CDCl_3$): δ9.9 (s, 1H), 8.4 (s, 1H), 7.2 (s, 1H), 7.1 (s, 1H), 7.0 (s, 1H), 4.4 (m, 1H), 3.0 (m, 1H), 1.6 (m, 4H), 1.2 (m, 4H), 1.0 (m, 6H) ppm.

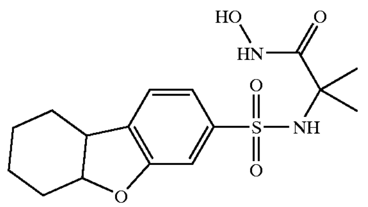

Additional compounds that can be made with the procedure for Examples 23 and 24 are the following:

EXAMPLE 25

1-(5a,6,7,8,9,9a-Hexahydro-dibenzofuran-3-sulfonylamino)-cyclopentane carboxylic acid

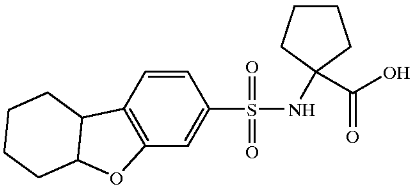

EXAMPLE 26

1-(5a,6,7,8,9,9a-Hexahydro-dibenzofuran-3-sulfonylamino)-cyclopentane carboxylic acid hydroxyamide

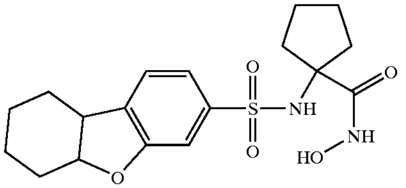

The next several examples were performed according to the general procedure shown and described below, in order to produce the indicated compounds. Initially, an aryl sulfonyl chloride ($ArSO_2Cl$) is reacted with an α, α'-disubstituted amino acid ester, using an inert solvent such as dichloromethane ($CH_2Cl_2$) and an acid scavenger such as triethylamine ($NEt_3$). The intermediate sulfonamide carboxylic acid ester is hydrolyzed with an aqueous base such as sodium hydroxide (NaOH), and then acidified with a suitable acid such as hydrochloric acid (HCl) to produce the amino acid sulfonamide, shown below. This carboxylic acid then can be converted to the hydroxamic acid by first generating the acid chloride using oxalyl chloride ($(COCl)_2$), or a similar chlorinating agent, and then reacting the intermediate acid chloride with a solution of free hydroxylamine.

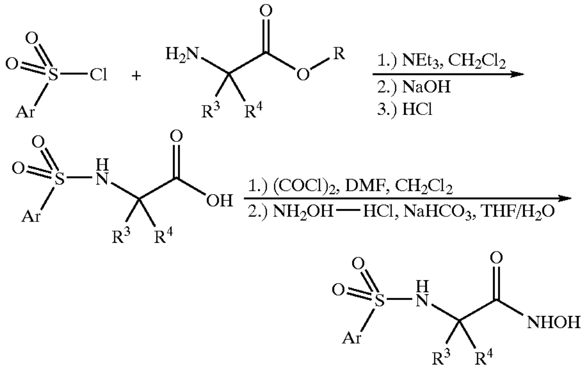

EXAMPLE 27

Synthesis of 1-(Dibenzofuran-3-sulfonylamino)-cyclohexanecarboxylic acid

Ethyl 1-aminocyclohexanecarboxylate (0.32 g, 1.9 mmol) and 0.5 g (1.9 mmol) of 3-dibenzofuran sulfonyl chloride were mixed in 50 mL of dichloromethane at room temperature. Excess triethylamine (0.78 mL, 5.7 mmol) was added, and the resulting mixture was stirred overnight. The reaction mixture was partitioned between 1 M HCl and dichloromethane. The dichloromethane layer was separated, and dried over magnesium sulfate, then concentrated. The residue was chromatographed to give 0.28 g of the ethyl ester of the 1-(dibenzofuran-3-sulfonylamino)-cyclohexanecarboxylic acid compound. This was suspended in 20 mL of 1 M NaOH and heated to reflux for 6 hours. The product was acidified with concentrated HCl and extracted with ethyl acetate. The ethyl acetate layer was dried over magnesium sulfate and concentrated to yield an off-white solid. The solid was triturated with 5% ethyl acetate/hexanes to give 0.20 g of the 1-(dibenzofuran-3-sulfonylamino)-cyclohexanecarboxylic acid compound, the structure of which is shown below, as a white solid. The compound had a melting point of about 239–243° C. $^1$HNMR ($CDCl_3$): δ7.97 (d, 1H), 7.90 (t, 2H), 7.77 (d, 1H), 7.49 (d, 1H), 7.41 (t, 1H), 7.27 (t, 1H), 6.31 (s, 1H), 1.75 (m, 4H), 1.23 (m, 6H) ppm. Analysis showed the compound to have an empirical formula of ($C_{19}H_{19}N_1O_5S$).

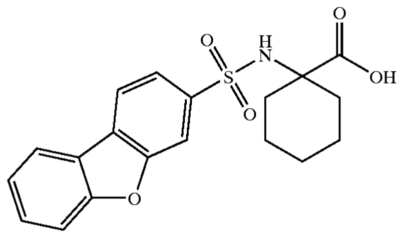

EXAMPLE 28

Synthesis of 1-(Dibenzofuran-3-sulfonylamino)-cyclohexanecarboxylic acid hydroxyamide 1-(Dibenzofuran-3-sulfonylamino)-cyclohexanecarboxylic acid (0.18 g, 0.5 mmol) was dissolved in 50 mL dichloromethane with 2 drops of dimethylformamide. Oxalyl chloride (0.08 mL, 1.0 mmol) was added, and the resulting solution was stirred for 2 hours, then concentrated in vacuo. The resulting residue was dissolved in 10 mL tetrahydrofuran, and this solution was added dropwise to a mixture of sodium bicarbonate (0.61 g, 7.2 mmol) and hydroxylamine hydrochloride (0.33 g, 4.8 mmol) in 50 mL of a tetrahydrofuran/water mixture (1:1 ratio) that had been stirring for 10 minutes at 0° C. The resulting mixture was allowed to warm to room temperature and stirred for 64 hours. The reaction was concentrated in vacuo and partitioned between 1 M HCl and dichloromethane. The aqueous layer was extracted with additional dichloromethane, followed by drying the combined organic layers over magnesium sulfate, filtration, and concentration to give 0.07 g of an off-white solid, the structure of which is shown below. The compound had a melting point of about 184–186° C. $^1$HNMR ($CDCl_3$): δ7.97 (d, 1H), 7.97 (s, 1H), 7.90 (dd, 2H), 7.75 (d, 1H), 7.48 (d, 1H), 7.41 (t, 1H), 7.27 (t, 1H), 6.65 (s, 1H), 1.79 (m, 4H), 1.14 (m, 6H) ppm. Analysis showed the compound to have an empirical formula of ($C_{19}H_{20}N_2O_5S.0.25H_2O$).

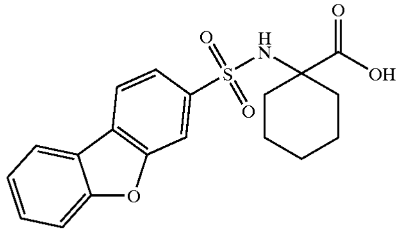

EXAMPLE 29

Synthesis of 2-(Dibenzofuran-3-sulfonylamino)-2-methyl-propionic acid

In the procedure of Example 27, ethyl 1-aminocyclohexanecarboxylate was replaced with α-aminoisobutyric acid methyl ester hydrochloride, and 2-(dibenzofuran-3-sulfonylamino)-2-methyl-propionic acid was obtained. The structure of this compound is identified below. The compound had a melting point of about 220–224° C. $^1$HNMR ($CDCl_3$): δ8.02 (s, 1H), 7.93 (dd, 2H), 7.83 (d, 1H), 7.53 (d, 1H), 7.46 (t, 1H), 7.31 (t, 1H), 6.26 (s, 1H), 1.36 (s, 6H) ppm. Analysis showed the compound to have an empirical formula of ($C_{16}H_{15}N_1O_5S.0.33H_2O$).

EXAMPLE 30

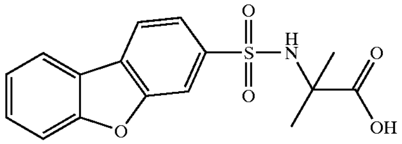

Synthesis of 2-(Dibenzofuran-3-sulfonylamino)-N-hydroxy-2-methyl-propionamide In the procedure of Example 28, 1-(dibenzofuran-3-sulfonylamino)-cyclohexanecarboxylic acid was replaced with 2-(dibenzofuran-3-sulfonylamino)-2-methyl-propionic acid, and 2-(dibenzofuran-3-sulfonylamino)-N-hydroxy-2-methyl-propionamide compound was obtained. The compound had a melting point of about 168–169° C. $^1$NMR ($CDCl_3$): δ7.96 (s, 1H), 7.87 (dd, 2H), 7.73 (d, 1H), 7.46 (d, 1H), 7.39 (t, 1H), 7.25 (t, 1H), 7.14 (s, 1H), 1.22 (s, 6H) ppm. Analysis showed the compound to have an empirical formula of ($C_{16}H_{16}N_2O_5S.1.25H_2O$). The structure of this compound is shown below.

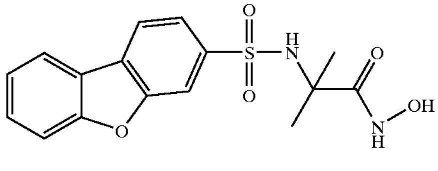

EXAMPLE 31

Synthesis of 4-(Dibenzofuran-3-sulfonylamino)-tetrahydro-pyran-4-carboxylic acid hydroxyamide In the procedure of Example 27, ethyl 1-aminocyclohexanecarboxylate was replaced with methyl 4-aminotetrahydro-2H-pyran-4-carboxylate, and 4-(dibenzofuran-3-sulfonylamino)-tetrahydro-pyran-4-carboxylic acid was obtained and used without further purification. In the procedure of Example 28, 1-(dibenzofuran-3-sulfonylamino)-cyclohexanecarboxylic acid was replaced with 4-(dibenzofuran-3-sulfonylamino)-tetrahydro-pyran-4-carboxylic acid, and the title compound is obtained. The compound had a melting point of about 160–162° C. Analysis showed the compound to have an empirical formula of ($C_{18}H_{18}N_2O_6S.2.5H_2O$). The structure of this compound is shown below.

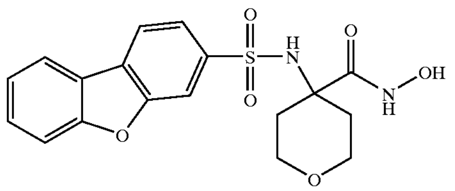

EXAMPLE 32

Synthesis of 1-(7-Bromo-dibenzofuran-2-sulfonylamino)-cyclopentane carboxylic acid hydroxamide When in the procedure of Example 28, 1-(dibenzofuran-3-sulfonylamino)-cyclohexane carboxylic acid was replaced with 1-(7-bromo-dibenzofuran-2-sulfonylamino)-cyclopentane carboxylic acid, and the title compound, shown below, was obtained. The compound had a melting point of 177–178° C.

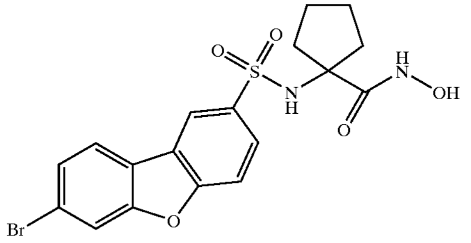

EXAMPLE 33

Synthesis of 2-(7-Chloro-dibenzofuran-2 sulfonylamino)-N-hydroxy-2-methyl-propionamide When in the procedure of Example 28, 1-(dibenzofuran-3-sulfonylamino)-cyclohexane carboxylic acid was replaced with 2-(7-chloro-dibenzofuran-2-sulfonylamino)-2-methyl-propionic acid, and the title compound, shown below was obtained. The compound had a melting point of 195–196° C.

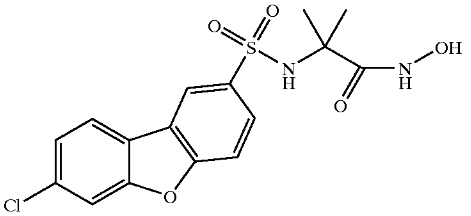

Biological Assays

The invention compounds have been evaluated in standard in vitro assays and have been shown to be potent inhibitors of a variety of matrix metalloproteinase enzymes. The compounds were evaluated in order to determine their respective $IC_{50}$ values, i.e., the micromolar concentration of compound required to achieve a 50% inhibition of the hydrolytic activity of the respective enzymes.

Experiments were carried out with the full-length ("FL") and/or catalytic domains ("CD") of the proteinases. Table 1 shows the activity of the compounds of Examples 27–31 versus MMP-1FL (collagenase-1 full-length enzyme), MMP-2CD (gelatinase A catalytic domain), MMP-2FL (gelatinase A full-length enzyme), MMP-3CD (stromelysin-1 catalytic domain), MMP-7FL (matrilysin full-length enzyme), MMP-9FL (gelatinase B full-length enzyme), MMP-13CD (collagenase-3 catalytic domain), and MMP-14CD (membrane-type MMP-1 catalytic domain). $IC_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli,*" *Biochemistry,* 1992;31:11231–11235; Ye Q.-Z., Johnson L. L., Yu A. E., and Hupe D., "Reconstructed 19 kDa Catalytic Domain of Gelatinase A IAAP," *Biochemistry,* 1995;34:4702–4708.)

The tested MMPs are available to those skilled in the art. For example, MMP-1 can be obtained from Washington University School of Medicine, St. Louis, Mo. MMP-7 can be obtained in accordance with the known procedure set forth by Ye Q. Z., Johnson L. L., and Baragi V., "Gene Syntheses and Expression in *E. coli* for PUMP, a Human Matrix Metalloproteinase," *Biochem. and Biophys. Res. Comm.,* 1992;186:143–149. MMP-13 can be obtained in accordance with the known procedure set forth by Freije J. M. P. et al., "Molecular Cloning and Expression of Collagenase-3, a Novel Human Matrix Metalloproteinase Produced by Breast Carcinomas," *J. Bio. Chem.,* 1994;269:16766–16773. MMP-13CD can also be expressed from a synthetic gene and purified from *Escherichia coli* cell culture according to a previously described method (Ye Q.-Z., Johnson L. L., and Baragi V., "Gene Synthesis and Expression in *E. coli* for PUMP, a Human Matrix Metalloproteinase," *Biochemical and Biophysical Research Communications,* 1992;186:143–149). Hydrolysis of the thiopeptolide substrate Ac-Pro-Leu-Gly-thioester-Leu-Leu-Gly-OEt (Bachem) was used as the primary screen to determine $IC_{50}$ values for MMP inhibitors. A 100 $\mu$L reaction contains 1 mM 5,5'-dithiobis(2-nitrobenzoic acid) (DTNB), 100 $\mu$M substrate, 0.1% BRIJ® 35, PROTEIN GRADE®, Detergent, 10% solution, Sigma, St. Louis, Mo. [polyoxyethyleneglycol dodecyl ether; polyoxyethylene (23) lauryl ether], enzyme, and inhibitor in the appropriate reaction buffer. Activated full-length enzymes are assayed at 5 nM, Stromelysin Catalytic Domain (SCD) at 10 nM, and Gelatinase A Catalytic Domain (GaCD) at 1 nM. Inhibitors are screened from 100 $\mu$M to 1 nM. Full-length enzymes (e.g., MMP-1 and MMP-7) are assayed in 50 mM 4-(2-hydroxymethyl)-piperazine-1-ethane sulfonic acid (HEPES), 10 mM $CaCl_2$, pH 7.0; SCD in 50 mM 2-morpholinoethane sulfonic acid monohydrate (MES), 10 mM $CaCl_2$, pH 6.0; and GaCD in 50 mM 3-morpholtriopropane sulfonic acid (MOPS), 10 mM $CaCl_2$, 10 $\mu$M $ZnCl_2$, pH 7.0. The change in absorbance at 405 nanometers is monitored on a ThermoMax microplate reader at room temperature continuously for 20 minutes.

The number in parenthesis indicates the number of samples assayed. Where multiple samples were assayed, the result presented in Table 1 is an average.

TABLE 1

| Compound of Ex. No. | Matrix Metalloproteinase Enzyme Inhibition IC$_{50}$ $\mu$M MMP 1 FL | MMP 2 CD | MMP 2 FL | MMP 3 CD | MMP 7 FL | MMP 9 FL | MMP 13 CD | MMP 14 CD |
|---|---|---|---|---|---|---|---|---|
| 27 | 1.75 (2) | 0.0027 (2) | 0.023 (2) | 0.00925 (2) | 4.25 (2) | 3.7 (2) | 0.23 (2) | 0.0265 (2) |
| 28 | 0.295 (2) | 0.0017 (2) | 0.0045 (2) | 0.0155 (2) | 4.05 (2) | 0.135 (2) | 0.049 (2) | 0.0039 (2) |
| 29 | 8.25 (2) | 0.00265 (2) | 0.0198 (2) | 0.00835 (2) | 34 (1) | 11.5 (2) | 0.45 (2) | 0.0225 (2) |
| 30 | 0.905 (2) | 0.0043 (2) | 0.00475 (2) | 0.0835 (2) | 100 (1) | 0.86 (2) | 0.105 (2) | 0.0135 (2) |
| 31 | 0.38 (2) | 0.0023 (2) | 0.00525 (2) | 0.01475 (2) | 3 (2) | 0.25 (2) | 0.048 (2) | 0.00575 (2) |
| 32 | 5.75 (2) | 0.08266 (3) | 0.205 (2) | 0.035 (2) | 0.35 (2) | 13 (1) | 0.165 (2) | 0.34 (2) |
| 33 | 3.05 (2) | 0.081 (3) | 0.125 (2) | 0.043 (2) | 0.92 (2) | 15 (1) | 0.11 (2) | 0.3 (2) |

When producing pharmaceutical compositions and preparations from the compounds of the present invention, pharmaceutically acceptable carriers can be either solid or liquid. Solid form preparations include powders, tablets, pills, capsules, cachets, suppositories, lozenges, and dispersible granules. A solid carrier can be one or more substances which also can act as diluents, flavoring agents, solubilizers, lubricants, suspending agents, binders, preservatives, tablet disintegrating agents, or an encapsulating material. The term "preparation" is intended to include the formulation of the active compound with encapsulating material as a carrier providing a capsule in which the active component, with or without other carriers, is surrounded by a carrier, which is thus in association with it.

In tablets and capsules, the active compound is admixed with at least one (a) inert excipient (or carrier), such as sodium citrate or dicalcium phosphate; (b) filler or extender, for example, a starch, lactose, sucrose, glucose, mannitol, and silicic acid; (c) a binder, for example, sorbitol, tragacanth, mucilage of starch, carboxymethylcellulose, alginates, gelatin, polyvinylpyrrolidone, sucrose, and acacia; (d) a humectant, for example, glycerol; (e) a disintegrating agent, for example, agar—agar, calcium carbonate, potato or tapioca starch, alginic acid, certain complex silicates, and sodium carbonate; (f) a solution retarder, for example paraffin; (g) an absorption accelerator, for example, quaternary ammonium compounds; (h) a wetting agent, for example, cetyl alcohol, sodium lauryl sulfate, and glycerol monostearate; (i) an adsorbent, for example, kaolin and bentonite; (j) a lubricant, for example, talc, calcium stearate, stearic acid, magnesium stearate, solid polyethylene glycols, sodium lauryl sulfate, sodium starch glycollate; and (k) mixtures thereof. In the case of capsules, tablets, and pills, the dosage forms also can comprise buffering agents.

Solid compositions of a similar type also can be employed as fillers in soft and hard-filled gelatin capsules using such excipients as lactose or milk sugar, as well as high molecular weight polyethyleneglycols, and the like.

Solid dosage forms such as tablets, dragees, capsules, pills, and granules can be prepared with coatings and shells, such as enteric coatings and others well-known in the art. The dosage form can contain opacifying agents, and also can be of such a design that the active compound or compounds is released in a predetermined part of the intestinal tract in a delayed manner. Examples of embedding compositions which can be used are polymeric substances and waxes. The active compounds can also be in micro-encapsulated form, if appropriate, with one or more of the above-mentioned excipients.

In powders, the carrier is a finely divided solid which is in a mixture with the finely divided active component. The powders and tablets preferably contain about five, preferably about 10 to about 70 percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

For preparing suppositories, a low melting wax, such as a mixture of the fatty acid glycerides, polyethylene glycol, or cocoa butter, is first melted and the active component is dispersed homogenously therein, as by stirring. The molten homogenous mixture is then poured into convenient sized molds, allowed to cool, and thereby to solidify.

Liquid form preparations include solutions, suspensions, emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired. The compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as (a) suspending agents (such as sorbitol syrup, methyl cellulose, glucose/sugar syrup, gelatin, hydroxyethylcellulose, hydroxypropyl methyl cellulose, carboxymethyl cellulose, aluminum stearate gel, ethoxylated isostearyl alcohols, polyoxyethylene sorbitol and sorbitan esters, microcrystalline cellulose, aluminum metahydroxide, bentonite, agar—agar, tragacanth, and hydrogenated edible fats), (b) emulsifying agents (such as lecithin, sorbitan monooleate, or acacia), (c) nonaqueous vehicles (which can include edible oils, such as almond oil, fractionated coconut oil, groundnut oil, corn germ oil, olive oil, castor oil, sesame oil, oily esters, propylene glycol, and ethyl alcohol), and (d) preservatives (such as methyl or propyl p-hydroxybenzoate, and sorbic acid). Aqueous suspensions suitable for oral use can be made by dispersing the finely divided active component in water with viscous material, such as natural or synthetic gums, resins, methylcellulose, sodium carboxymethylcellulose, and other well-known suspending agents.

These compositions also can contain adjuvants such as preserving, wetting, emulsifying, suspending, and dispensing agents, as well as sweetening, flavoring, and perfuming agents. Prevention of action by microorganism can be provided by various antibacterial and antifungal agents, for example, parabens, chlorobutanol, phenol, sorbic acid, and the like. It also may be desirable to include isotonic agents, for example sugars, sodium chloride, and the like. Prolonged absorption of the injectable pharmaceutical form can be brought about by the use of agents delaying absorption, for example, aluminum monostearate and gelatin.

The following examples illustrate typical formulations provided by the invention.

EXAMPLE 34

Tablet Formulation

| Ingredient | Amount (mg) |
|---|---|
| Active Compound of Example 3 | 25 |
| Lactose | 50 |
| Corn starch | 10 |
| Corn starch (paste) | 10 |
| Magnesium stearate (1 weight %) | 5 |
| | 100 |

To produce a tablet of the invention, the active compound, lactose, and corn starch preferably are blended to provide a uniform mixture. The corn starch (for paste) is suspended in 200 mL of water and heated with stirring to form a paste. The paste is used to granulate the mixed powders. The wet granules are passed through a No. 8 hand screen and dried at about 80° C. The dry granules are lubricated with the 1% magnesium stearate and pressed into a tablet by conventional apparatus. Such tablets can be administered to a human from one to about four times per day for treatment of atherosclerosis and arthritis, for example.

EXAMPLE 35

Preparation for Oral Solution

| Ingredient | Amount |
|---|---|
| Active Compound of Example 14 | 400 mg |
| Sorbitol Solution (70% N.F.) | 40 mL |
| Sodium Benzoate | 20 mg |
| Saccharin | 5 mg |
| Red Dye | 10 mg |
| Cherry Flavor | 20 mg |
| Distilled Water q.s. | 100 mL |

To produce an oral solution of the invention, the sorbitol solution is added to 40 mL of distilled water, and the active compound of the invention is dissolved therein. The saccharin, sodium benzoate, flavor, and dye are added and dissolved. The volume is adjusted to 100 mL with distilled water. Each milliliter of syrup contains about 4 mg of the inventive compound.

EXAMPLE 36

| Ingredient | Amount |
|---|---|
| Propylene glycol | 700 mL |
| Water for injection | 200 mL |
| Active Compound of Example 28 | 20 g |
| NaOH (IN) | to pH 6.5 |
| Water for injection | to 1000 mL |

Parenteral Solution

In a solution of 700 mL of propylene glycol and 200 mL of water for injection is suspended 20 g of an active hydroxamic acid compound of the invention. After suspension is complete, the pH is adjusted to about 6.5 with 1N sodium hydroxide, and the volume is made up to 1000 mL with water for injection. The formulation is sterilized, filled into 5.0 mL ampoules each containing 2.0 mL, and sealed under nitrogen.

As matrix metalloproteinase inhibitors, the compounds of Formula I are useful as agents in the treatment of multiple sclerosis. They are also useful as agents for the treatment of osteoporosis, renal disease, atherosclerotic plaque rupture, heart failure, aortic aneurism, left ventricular dilatation, thrombosis, restenosis, periodontal disease, corneal ulceration, treatment of burns, decubital ulcers, chronic ulcers, wound repair, strokes, cancer metastasis, tumor angiogenesis, arthritis, including rheumatoid arthritis and osteoarthritis and autoimmune or inflammatory disorders including those dependent upon tissue invasion by leukocytes. These compounds are also useful as agents in the treatment of chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy. These compounds also can be used during and after surgical procedures, e.g., artery bypass and hip operations, as well as angioplasty.

The foregoing detailed description is given for clearness of understanding only, and no unnecessary limitations should be understood therefrom, as modifications within the scope of the invention will be apparent to those skilled in the art.

What is claimed is:

1. A compound of the Formula I

I

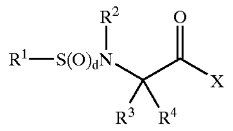

or a pharmaceutically acceptable salt thereof, wherein X is selected from OH and NHOH; d is 1 or 2;

$R^1$ is selected from the group consisting of:

(a)

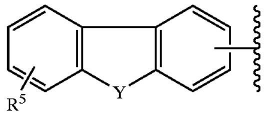

wherein Y is selected from the group consisting of O;

$R^5$ is selected from the group consisting of H, $C_{1-10}$ alkyl, $CF_3$, $CONH_2$, halo, CN, COOH, $C_{1-4}$ alkoxy, CHO, $NO_2$, OH, $(CH_2)_pOH$, $(CH_2)_pNH_2$, Ar, and $NH_2$;

$R^2$ is selected from the group consisting of (a) hydrogen; (b) $C_{1-4}$ alkyl; (c) benzyl; and (d) benzyl substituted with one or more of $C_{1-4}$ alkyl, $C_{1-4}$ alkoxy, F, Cl, Br, I, $NH_2$, $NO_2$, CN, carboxy, and $CO_2R^7$ (where $R^7$ is H or $C_{1-4}$ alkyl); and $R^3$ and $R^4$ are either (1) each independently selected from the group consisting of $C_{1-20}$ alkyl; $C_{3-10}$ cycloalkyl; phenyl; phenyl substituted with $C_{1-4}$ alkyl, $C_{1-4}$ alkoxy, halo, $NH_2$, $NO_2$, CN, COOH, $CO_2R^7$, or $CF_3$; $C_{3-10}$ heterocyclic; and heteroaryl; or (2) substituents taken together to form a group of the empirical formula $-(CH_2)_sZ_g-$, wherein said substituents form a ring including the carbon atom adjacent the carbonyl group in Formula I, and wherein s is an integer from 2 to 10; g is 0 to 6; and each Z is located at any position of said substituents and each Z is independently selected from the group consisting of O, S, and $NR^8$ (where $R^8$ is selected from H and $C_{1-3}$ alkyl).

2. The compound of claim 1, wherein $R^1$ is selected from the group consisting of:

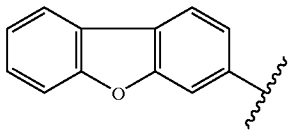

and

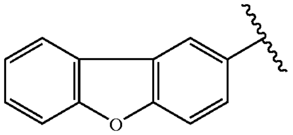

.

3. The compound of claim 1, wherein $R^2$ is hydrogen, $R^3$ is a methyl group, and $R^4$ is a methyl group.

4. The compound of claim 1, wherein $R^3$ and $R^4$ are taken together as $-(CH_2)_s-$ (where s, the total number of carbon atoms from both $R^3$ and $R^4$, is from 2 to 10) to form a ring including the alpha carbon atom adjacent the carbonyl group in Formula I.

5. The compound of claim 4, where s equals 4 or 5.

6. The compound of claim 4, wherein said ring includes a heteroatom selected from the group consisting of nitrogen, oxygen, and sulfur.

7. The compound of claim 1, wherein $R^3$ and $R^4$ are taken together to form a ring including the carbon atom adjacent the carbonyl group in Formula I, and together $R^3$ and $R^4$ are selected from the group consisting of:

$-CH_2CH_2CH_2CH_2-$, $-CH_2CH_2CH_2CH_2CH_2-$, and $-CH_2CH_2OCH_2CH_2-$.

8. The compound of claim 1 wherein $R^3$ and $R^4$ are taken together to form a ring including the alpha carbon atom adjacent the carbonyl group in Formula I, and together $R^3$ and $R^4$ are selected from the group consisting of:

$-CH_2CH_2-$, $-CH_2CH_2CH_2-$, $-CH_2CH_2CH_2CH_2-$, $-CH_2CH_2CH_2CH_2CH_2-$, $-CH_2CH_2CH_2CH_2CH_2CH_2-$, $-CH_2OCH_2CH_2-$, $-CH_2CH_2OCH_2CH_2-$, $-CH_2CH_2OCH_2CH_2CH_2-$, $-CH_2N(H)CH_2CH_2-$, $-CH_2CH_2N(H)CH_2CH_2-$, $-CH_2CH_2N(H)CH_2CH_2CH_2-$, $-CH_2SCH_2CH_2-$, $-CH_2CH_2SCH_2CH_2-$, $-CH_2CH_2SCH_2CH_2CH_2-$, $-CH_2OCH_2CH_2OCH_2-$, $-CH_2N(H)CH_2CH_2N(H)CH_2-$, and $-CH_2SCH_2CH_2SCH_2-$, wherein the terminal carbons are both bonded to the alpha carbon atom adjacent the carbonyl group in Formula I.

9. The compound of claim 1, wherein the compound is selected from the group consisting of:

1-(Dibenzofuran-3-sulfonylamino)-cyclohexanecarboxylic acid;

1-(Dibenzofuran-3-sulfonylamino)-cyclohexanecarboxylic acid hydroxyamide;

2-(Dibenzofuran-3-sulfonylamino)-2-methyl-propionic acid;

2-(Dibenzofuran-3-sulfonylamino)-N-hydroxy-2-methyl-propionamide;

4-(Dibenzofuran-3-sulfonylamino)-tetrahydro-pyran-4-carboxylic acid hydroxyamide;

1-(7-Bromo-dibenzofuran-2-sulfonylamino)-cyclopentane carboxylic acid hydroxyamide; and 2-(7-Chloro-dibenzofuran-2-sulfonylamino)-N-hydroxy-2-methyl-propionamide.

10. A pharmaceutical formulation comprising a compound of claim 1 admixed with a diluent, carrier, or excipient therefor.

* * * * *